US011783265B2

(12) United States Patent
Wilkerson et al.

(10) Patent No.: US 11,783,265 B2
(45) Date of Patent: Oct. 10, 2023

(54) SCORE CARDS

(71) Applicant: CERNER INNOVATION, INC., Kansas City, KS (US)

(72) Inventors: Benjamin David Wilkerson, Lee's Summit, MO (US); Kevin Krizek, Kansas City, KS (US); Patrick O'Brien, Kansas City, KS (US); Bharat Sutariya, Parkville, MO (US)

(73) Assignee: CERNER INNOVATION, INC., Kansas City, MO (US)

(*) Notice: Subject to any disclaimer, the term of this patent is extended or adjusted under 35 U.S.C. 154(b) by 438 days.

(21) Appl. No.: 16/418,270

(22) Filed: May 21, 2019

(65) Prior Publication Data
US 2019/0279135 A1  Sep. 12, 2019

Related U.S. Application Data

(63) Continuation of application No. 14/048,398, filed on Oct. 8, 2013, now Pat. No. 10,332,055.

(60) Provisional application No. 61/710,877, filed on Oct. 8, 2012.

(51) Int. Cl.
*G16H 40/20* (2018.01)
*G06Q 10/0639* (2023.01)
*G16H 10/60* (2018.01)
*G16H 40/67* (2018.01)
*G06Q 30/0201* (2023.01)

(52) U.S. Cl.
CPC .. *G06Q 10/06393* (2013.01); *G06Q 10/06395* (2013.01); *G06Q 30/0201* (2013.01); *G16H 10/60* (2018.01); *G16H 40/20* (2018.01); *G16H 40/67* (2018.01)

(58) Field of Classification Search
CPC .................. G06Q 50/22–24; G16H 40/20
See application file for complete search history.

(56) References Cited

U.S. PATENT DOCUMENTS

| 5,664,109 A | 9/1997 | Johnson et al. |
| 2002/0111826 A1 | 8/2002 | Potter et al. |
| 2004/0168115 A1 | 8/2004 | Bauernschmidt et al. |
| 2005/0209869 A1* | 9/2005 | Irvin ................ G06Q 10/0835 705/336 |
| 2006/0282286 A1* | 12/2006 | Faris, III ............... G06N 5/043 706/45 |
| 2007/0067199 A1 | 3/2007 | Shine et al. |

(Continued)

OTHER PUBLICATIONS

"Quality Measures" CMS.gov (Year: 2020).*

(Continued)

*Primary Examiner* — John A Pauls
(74) *Attorney, Agent, or Firm* — KRAGULJAC LAW GROUP, LLC

(57) ABSTRACT

Methods, systems, and computer-readable media are provided for building a score plan for a healthcare organization, its providers, its payers, and/or its patients and presenting the results of the score plan on one or more score card user interfaces. Score cards graphically display an entity's progress towards meeting quality measure objectives. The score cards provide information on percentage completion of one or more quality measure objectives by the entity and/or quality measure objectives that may be difficult for the entity to achieve.

20 Claims, 24 Drawing Sheets

(56) References Cited

U.S. PATENT DOCUMENTS

| | | | |
|---|---|---|---|
| 2008/0015896 A1* | 1/2008 | Reynolds | G06Q 10/10 705/2 |
| 2008/0059292 A1* | 3/2008 | Myers | G06Q 50/10 705/7.39 |
| 2008/0201174 A1 | 8/2008 | Ramasubramanian et al. | |
| 2009/0172773 A1 | 7/2009 | Moore | |
| 2009/0281826 A1 | 11/2009 | Zak et al. | |
| 2010/0174557 A1 | 7/2010 | Bundschus et al. | |
| 2010/0235192 A1 | 9/2010 | George et al. | |
| 2012/0053995 A1* | 3/2012 | D'Albis | G06Q 10/10 705/7.39 |
| 2012/0130730 A1* | 5/2012 | Setlur | G16H 40/20 705/2 |
| 2012/0253836 A1 | 10/2012 | Nolte et al. | |
| 2012/0253886 A1 | 10/2012 | Nelson et al. | |
| 2014/0032240 A1 | 1/2014 | Lougheed et al. | |
| 2014/0100866 A1 | 4/2014 | Wilkerson et al. | |
| 2014/0122100 A1 | 5/2014 | Fillmore | |
| 2015/0012298 A1 | 1/2015 | Ash et al. | |
| 2015/0248532 A1* | 9/2015 | Rajasenan | G16H 40/20 705/2 |

OTHER PUBLICATIONS

Final Office Action received for U.S. Appl. No. 14/453,864, dated Nov. 2, 2017, 20 pages.
Final Office Action received for U.S. Appl. No. 14/048,349, dated Jun. 5, 2017, 22 pages.
Final Office Action received for U.S. Appl. No. 14/048,349, dated Oct. 20, 2016, 23 pages.
Final Office Action received for U.S. Appl. No. 14/048,365, dated Oct. 20, 2016, 20 pages.
Final Office Action received for U.S. Appl. No. 14/048,377, dated Oct. 20, 2016, 22 pages.
Final Office Action received for U.S. Appl. No. 14/048,377, dated Sep. 21, 2017, 21 pages.
Final Office Action received for U.S. Appl. No. 14/048,390, dated Feb. 11, 2016, 17 pages.
Final Office Action received for U.S. Appl. No. 14/048,390, dated May 13, 2016, 18 pages.
Final Office Action received for U.S. Appl. No. 14/048,398, dated Jan. 25, 2018, 17 pages.
Final Office Action received for U.S. Appl. No. 14/048,398, dated Nov. 3, 2016, 28 pages.
First Action Interview Office Action received for U.S. Appl. No. 14/048,349, dated May 18, 2016, 4 pages.
First Action Interview Office Action received for U.S. Appl. No. 14/048,365, dated May 19, 2016, 4 pages.
First Action Interview Office Action received for U.S. Appl. No. 14/048,390, dated Nov. 18, 2015, 5 pages.
First Action Interview Office Action received for U.S. Appl. No. 14/048,398, dated Jun. 2, 2016, 5 pages.
First Action Interview Office Action received for U.S. Appl. No. 14/453,864, dated Apr. 21, 2017, 5 pages.
First Action Interview Office Action received for U.S. Appl. No. 14/048,377, dated May 13, 2016, 4 pages.
Non-Final Office Action received for U.S. Appl. No. 14/048,390, dated Dec. 20, 2017, 35 pages.
Non-Final Office Action received for U.S. Appl. No. 14/048,398, dated Oct. 5, 2018, 17 pages.
Non-Final Office Action received for U.S. Appl. No. 14/048,349, dated Feb. 14, 2017, 20 pages.
Non-Final Office Action received for U.S. Appl. No. 14/048,377 dated Feb. 9, 2017, 23 pages.
Non-Final Office Action received for U.S. Appl. No. 14/048,398, dated Jul. 13, 2017, 19 pages.
Notice of Allowance received for U.S. Appl. No. 14/048,398, dated Mar. 1, 2019, 8 pages.
Preinterview First Office Action of U.S. Appl. No. 14/048,349 dated Dec. 4, 2015, 4 pages.
Preinterview First Office Action of U.S. Appl. No. 14/048,365 dated Dec. 4, 2015, 4 pages.
Preinterview First Office Action of U.S. Appl. No. 14/048,377 dated Dec. 4, 2015, 4 pages.
Preinterview First Office Action of U.S. Appl. No. 14/048,390 dated Sep. 11, 2015, 4 pages.
Preinterview First Office Action of U.S. Appl. No. 14/048,398 dated Dec. 9, 2015, 4 pages.
Preinterview First Office Action of U.S. Appl. No. 14/453,864 dated Nov. 4, 2016, 4 pages.
United States Patent and Trademark Office, Final Office Action issued in U.S. Appl. No. 16/235,725 (Filing date: Dec. 28, 2018) having a Notification dated Jun. 6, 2023 (8 pgs).

* cited by examiner

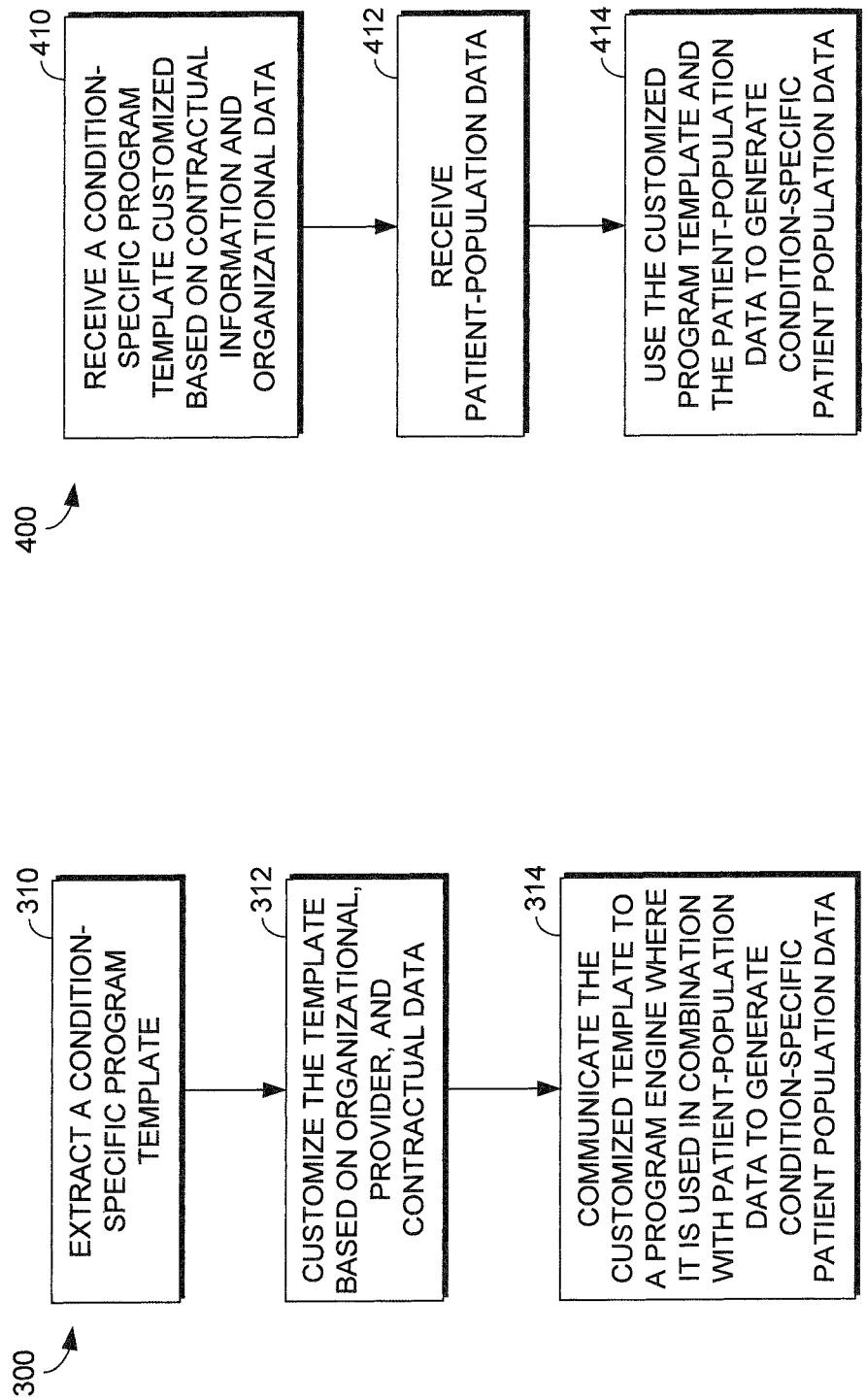

FIG. 17.

BEST PLAN EVER   STATUS: DRAFT   TYPE: PROVIDER   START DATE: 1/1/2014   END DATE: 1/1/2015

CREATE CATEGORIES AND MEASURES

| * PATIENT WELLNESS — 1810 | MEASURES |
|---|---|

🔍 SEARCH MEASURES

| 30 DAY READMISSION RATE – ALL CAUSE – HOS...<br>30 DAY READMISSION RATE | ADD |
| ADMIT DECISION TIMET TO ED DEPARTURE FO....<br>EMERGENCY DEPARTMENT CORE MEASURES | ADD |
| ADULT WELLNESS ALCOHOL ASSESSMENT<br>ADULT WELLNESS | ADD |
| ADULT WELLNESS BLOOD PRESSURE MEASUR... 1814<br>ADULT WELLENSS | ADD |
| ADULT WELLNESS BMI FOLLOW UP PLAN 1816<br>ADULT WELLNESS | ADD |
| ADULT WELLNESS BMI MEASUREMENTS<br>ADULT WELLNESS | ADD |
| ADULT WELLNESS EXERCISE ASSESSMENT A...<br>ADULT WELLNESS | ADD |
| ALOS<65 – MODERATELY MANAGED – INDIVID...<br>AVERAGE LENGTH OF STAY < 65 YEARS OF AGE | ADD |
| ALOS<65 – MODERATELY MANAGED – PRACT...<br>AVERAGE LENGTH OF STAY < 65 YEARS OF AGE | ADD |
| ALOS<65 – WELL MANAGED – INDIVIDUAL...<br>AVERAGE LENGTH OF STAY < 65 YEARS OF AGE | ADD |

1812

BACK   STEP 3   DONE

BEST PLAN EVER    STATUS: DRAFT    TYPE: PROVIDER    START DATE: 1/1/2014    END DATE: 1/1/2015

CREATE CATEGORIES AND MEASURES

MEASURES

- ADULT WELLNESS BMI FOLLOW UP... ADULT WELLNESS    [REMOVE] — 1814
- ADULT WELLNESS BMI MEASUREM... ADULT WELLNESS    [REMOVE] — 1816

🔍 SEARCH MEASURES

| | |
|---|---|
| 30 DAY READMISSION RATE – ALL CAUSE – HOS... 30 DAY READMISSION RATE | [ADD] |
| ADMIT DECISION TIMET TO ED DEPARTURE FO... EMERGENCY DEPARTMENT CORE MEASURES | [ADD] |
| ADULT WELLNESS ALCOHOL ASSESSMENT ADULT WELLNESS | [ADD] |
| ADULT WELLNESS BLOOD PRESSURE MEASUR... ADULT WELLENSS | [ADD] |
| ADULT WELLNESS EXERCISE ASSESSMENT A... ADULT WELLNESS | [ADD] |
| ALOS<65 – MODERATELY MANAGED – INDIVID... AVERAGE LENGTH OF STAY < 65 YEARS OF AGE | [ADD] |
| ALOS<65 – MODERATELY MANAGED – PRACT... AVERAGE LENGTH OF STAY < 65 YEARS OF AGE | [ADD] |
| ALOS<65 – WELL MANAGED – INDIVIDUAL... AVERAGE LENGTH OF STAY < 65 YEARS OF AGE | [ADD] |
| ALOS<65 – WELL MANAGED – PRACTICE GROU... AVERAGE LENGTH OF STAY < 65 YEARS OF AGE | [ADD] |
| ALOS>=65 – MODERATELY MANAGED –... AVERAGE LENGTH OF STAY >= 65 YEARS OF AGE | [ADD] |

1812

PATIENT WELLNESS — 1810 ⊕

[BACK]    [STEP 3]    [DONE]

BEST PLAN EVER    STATUS: DRAFT    TYPE: PROVIDER    START DATE: 1/1/2014    END DATE: 1/1/2015

MANAGE POINTS AND WEIGHT — 2012

▼ HBA1C < 7% — 2014
   DIABETES WELLNESS

| | | MIN. NUMBER OF PATIENTS | | | |
|---|---|---|---|---|---|
| PROVIDERS – FOR PROVIDERS | | 45 | POINTS | CALCULATED PERCENTAGE OF TOTAL SCORE 0 | WITH CREDIT BELOW MINIMUM — 2124 |
| FOR ALL | >= 70% | | | | |
| FOR ENDOCRINOLOGISTS | >= 30% | 2122 | POINTS | CALCULATED PERCENTAGE OF TOTAL SCORE 0 | |
| ST. JOHN'S | | MIN. NUMBER OF PATIENTS 45 | POINTS | CALCULATED PERCENTAGE OF TOTAL SCORE 0 | WITH CREDIT BELOW MINIMUM — 2128 |
| FOR PROVIDERS | >= 30% | 2126 | | | |

▲ HBA1A < 8%
   DIABETES WELLNESS

▲ HBA1A < 9%
   DIABETES WELLNESS

▲ LDL SCREENING
   DIABETES WELLNESS

▲ LDL <100 MG/DL
   DIABETES WELLNESS 1810    2130

PATIENT WELLNESS WEIGHT [ ]

2018
2024

BACK    FINISH    DONE

BEST PLAN EVER    STATUS: DRAFT    TYPE: PROVIDER    START DATE: 1/1/2014    END DATE: 1/1/2015

MANAGE POINTS AND WEIGHT

▼ HBA1C < 7%  — 2012
  DIABETES WELLNESS  — 2014

| PROVIDERS – FOR PROVIDERS | MIN. NUMBER OF PATIENTS | 45 | | | CALCULATED PERCENTAGE OF TOTAL SCORE | 2 | WITH CREDIT BELOW MINIMUM |
|---|---|---|---|---|---|---|---|
| FOR ALL | >= 70% | | POINTS | 2 | | | |
| FOR ENDOCRINOLOGISTS | >= 30% | | POINTS | 2 | CALCULATED PERCENTAGE OF TOTAL SCORE | 20 | — 2124 |

ST. JOHN'S

| | MIN. NUMBER OF PATIENTS | 45 | | | CALCULATED PERCENTAGE OF TOTAL SCORE | 2 | WITH CREDIT BELOW MINIMUM |
|---|---|---|---|---|---|---|---|
| FOR PROVIDERS | >= 30% | | POINTS | 2 | — 2126 | — 2128 | |

▲ HBA1A < 8%
  DIABETES WELLNESS

▲ HBA1A < 9%
  DIABETES WELLNESS

▲ LDL SCREENING
  DIABETES WELLNESS

▲ LDL <100 MG/DL
  DIABETES WELLNESS 1810  2130
PATIENT WELLNESS
WEIGHT: 4
— 2018
— 2024

BACK    FINISH    DONE

| BEST PLAN EVER | STATUS: DRAFT | TYPE: PROVIDER | START DATE: 1/1/2014 | END DATE: 1/1/2015 | |
|---|---|---|---|---|---|
| | | | | VIEWING: | ALL ▾ |
| | | | | | FOR AWESOME PEOPLE |
| ▼ HBA1C < 7% | | | | | FOR SOPHISTICATED PEOPLE |
| DIABETES WELLNESS | | | | | PRACTICE |
| | | | | | PRACTICE |
| PROVIDERS | | MIN. NUMBER OF PATIENTS 45 | | WITH | PRACTICE |
| | | | | | PRACTICE |
| FOR ALL GROUPS | | | | | PRACTICE |
| FOR CARDIOLOGISTS > = 70% | | 2 POINTS | CALCULATED PERC | | PRACTICE |
| FOR <GROUP> > = 70% | | 2 POINTS | CALCULATED PERC | | PRACTICE |
| FOR <GROUP> > = 70% | | 2 POINTS | CALCULATED PERC | | PROVIDER |
| FOR <GROUP> > = 70% | | 2 POINTS | CALCULATED PERC | | PROVIDER |
| FOR <GROUP> > = 70% | | 2 POINTS | CALCULATED PERC | | PROVIDER |
| FOR <GROUP> > = 70% | | 2 POINTS | CALCULATED PERCENT OF TOTAL SCORE 2 | | |
| ST. JOHN'S | | MIN. NUMBER OF PATIENTS 45 | | WITH CREDIT BELOW MINIMUM | |
| FOR PROVIDERS > = 30% | | 2 POINTS | CALCULATED PERCENT OF TOTAL SCORE 2 | | |
| ▲ HBA1A < 8% | | | | | |
| DIABETES WELLNESS | | | | | |

PATIENT WELLNESS WEIGHT: 4

BACK   CONFIRM   DONE

*FIG. 23.*

SCORE CARDS

CROSS-REFERENCE TO RELATED APPLICATIONS

This application is a continuation of U.S. Pat. No. 10,332,055, filed on 8 Oct. 2013 and entitled "Score Cards," which claims the benefit of and priority to U.S. Provisional App. No. 61/710,877, filed Oct. 8, 2012 and entitled "Organizational Management of Population Health," all of which are incorporated herein in their entireties by reference.

Additionally, U.S. Pat. No. 10,332,055, filed on 8 Oct. 2013 and entitled "Score Cards," is related by subject matter to: U.S. application Ser. No. 14/048,365, filed on 8 Oct. 2013 and entitled "Provider and Patient Attribution Programs;" U.S. application Ser. No. 14/048,377, filed on 8 Oct. 2013 and entitled "Contracts and Organization Management Program;" U.S. application Ser. No. 14/048,390, filed on 8 Oct. 2013 and entitled "Outreach Program;" and U.S. application Ser. No. 14/048,349, filed on 8 Oct. 2013 and entitled "Organizational Population Health Management Platform and Programs;" all of which are hereby incorporated herein in their entirety by reference.

BRIEF SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In brief and at a high level, this disclosure describes, among other things, methods, systems, computer storage media, and graphical user interfaces for organizational management of population health. A system or platform for managing population health includes a network management service that builds, maintains, and updates data stores that include information about healthcare organizations, healthcare providers, and information concerning contractual provisions between healthcare organizations and payers (e.g., insurance companies). The network management service also includes a program builder that builds condition-specific and/or objective-specific program templates. The program templates are designed to, among other things, identify population segments based on condition or purpose, stratify the population segment using different factors, generate workflows, attribute patients within the segment to healthcare providers, manage healthcare organizations and contracts, measure intervention outcomes, and the like.

The system further includes a population management service that builds, maintains, and updates data stores that include longitudinal patent-centric information drawn from a variety of disparate data sources. Such information may include demographic information, claims information, pharmacy information, clinical care information, socioeconomic information, financial information, and the like. Additionally, the system includes a compiler that extracts a program template and customizes or localizes it based on a particular healthcare organization's organizational and provider information as well as the particular contractual provisions associated with the healthcare organization and its associated payers.

At run-time, a program engine in the system uses the customized program templates and the patient population information from the population management service to generate condition-specific or objective-specific patient population data for the healthcare organization. This data is used by the healthcare organization to, among other things, identify patient segments based on a condition or for a specific purpose, stratify patients within the segment by degree of risk, generate interventions, attribute patients in the segment to healthcare providers associated with the particular healthcare organization, measure intervention outcomes, manage payer/organization contracts, determine provider incentives, and the like.

BRIEF DESCRIPTION OF THE DRAWINGS

Embodiments are described in detail below with reference to the attached drawing figures, wherein:

FIGS. 3-4 are flow diagrams illustrating exemplary methods of managing population health at a healthcare organization level in accordance with embodiments of the present invention;

FIGS. 17-23 depict exemplary user interfaces for building score plans for a healthcare organization, a provider, a payer, and a patient in accordance with embodiments of the present invention;

DETAILED DESCRIPTION

Figure 1:
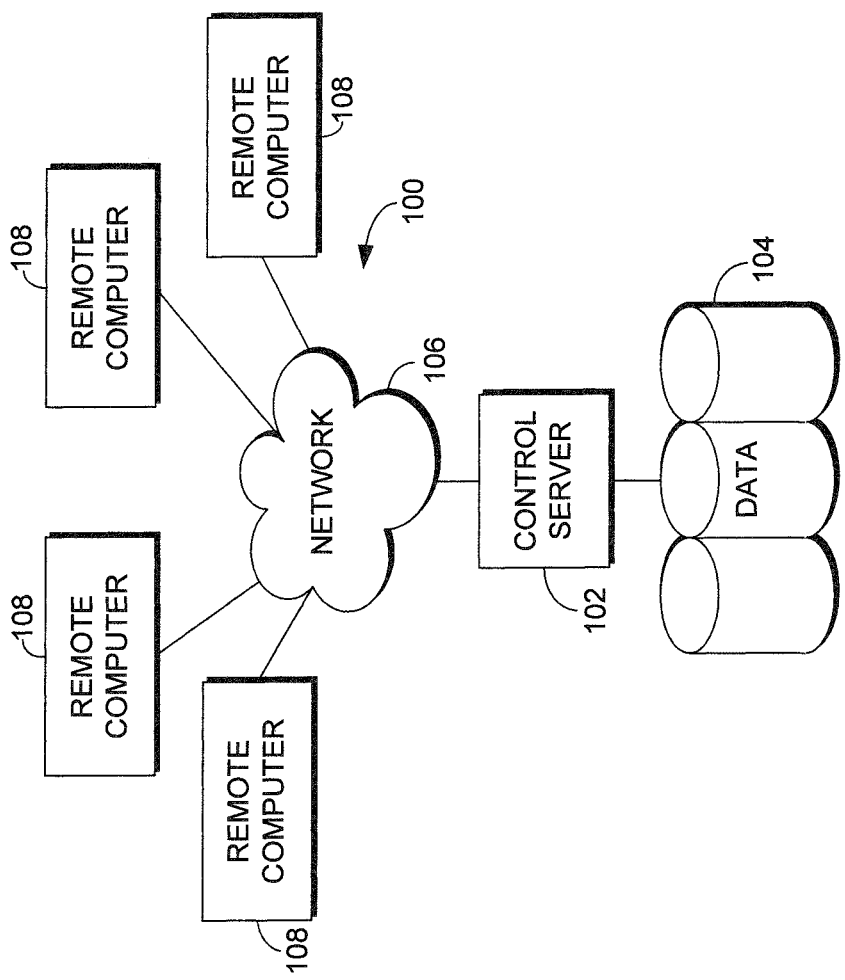
FIG. 1 is a block diagram of an exemplary computing environment suitable to implement embodiments of the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

In brief and at a high level, this disclosure describes, among other things, methods, systems, computer storage media, and graphical user interfaces for organizational management of population health. A system or platform for managing population health includes a network management service that builds, maintains, and updates data stores that include information about healthcare organizations, healthcare providers, and information concerning contractual provisions between healthcare organizations and payers (e.g., insurance companies). The network management service also includes a program builder that builds condition-specific and/or objective-specific program templates. The program templates are designed to, among other things, identify population segments based on condition or purpose, stratify the population segment using different factors, generate workflows, attribute patients within the segment to healthcare providers, manage organization and contracts, generate outreach events, measure intervention outcomes, and the like.

The system further includes a population management service that builds, maintains, and updates data stores that include longitudinal patent-centric information drawn from a variety of disparate data sources. Such information may include demographic information, financial information, socioeconomic information, claims information, pharmacy information, clinical care information, and the like. Additionally, the system includes a compiler that extracts a program template and customizes or localizes it based on a particular healthcare organization's organizational and provider information as well as the particular contractual provisions associated with the healthcare organization and its associated payers.

At run-time, a program engine in the system uses the customized program templates and the patient population information from the population management service to generate condition-specific or objective-specific patient population data for the healthcare organization. This data is used by the healthcare organization to, among other things, identify patient segments based on a condition or for a specific purpose, stratify patients within the segment by degree of risk, generate interventions, attribute patients in the segment to healthcare providers associated with the particular healthcare organization, measure intervention outcomes, manage payer/organization contracts, determine provider incentives, generate outreach events, and the like.

An exemplary computing environment suitable for use in implementing embodiments of the present invention is described below. FIG. 1 is an exemplary computing environment (e.g., medical-information computing-system environment) with which embodiments of the present invention may be implemented. The computing environment is illustrated and designated generally as reference numeral 100. The computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein.

The present invention might be operational with numerous other purpose computing system environments or configurations. Examples of well-known computing systems, environments, and/or configurations that might be suitable for use with the present invention include personal computers, server computers, hand-held or laptop devices, multi-processor systems, microprocessor-based systems, set top boxes, programmable consumer electronics, network PCs, minicomputers, mainframe computers, distributed computing environments that include any of the above-mentioned systems or devices, and the like.

The present invention might be described in the general context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 comprises a computing device in the form of a control server 102. Exemplary components of the control server 102 comprise a processing unit, internal system memory, and a suitable system bus for coupling various system components, including data store 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102 typically includes therein, or has access to, a variety of non-transitory computer-readable media. Computer-readable media can be any available media that might be accessed by control server 102, and includes volatile and nonvolatile media, as well as, removable and nonremovable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 102. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and clinicians' offices. Clinicians or healthcare providers may comprise a treating physician or physicians; specialists such as surgeons, radiologists, cardiologists, and oncologists; emergency medical technicians; physicians' assistants; nurse practitioners; health coaches; nurses; nurses' aides; pharmacists; dieticians; microbiologists; laboratory experts; laboratory technologists; genetic counselors; researchers; veterinarians; students; and the like. The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server 102, the data store 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a pointing device (commonly referred to as a mouse), a trackball, or a touch pad. Other input devices comprise microphones, satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

Although many other internal components of the control server 102 and the remote computers 108 are not shown, such components and their interconnection are well known. Accordingly, additional details concerning the internal construction of the control server 102 and the remote computers 108 are not further disclosed herein.

Figure 2:
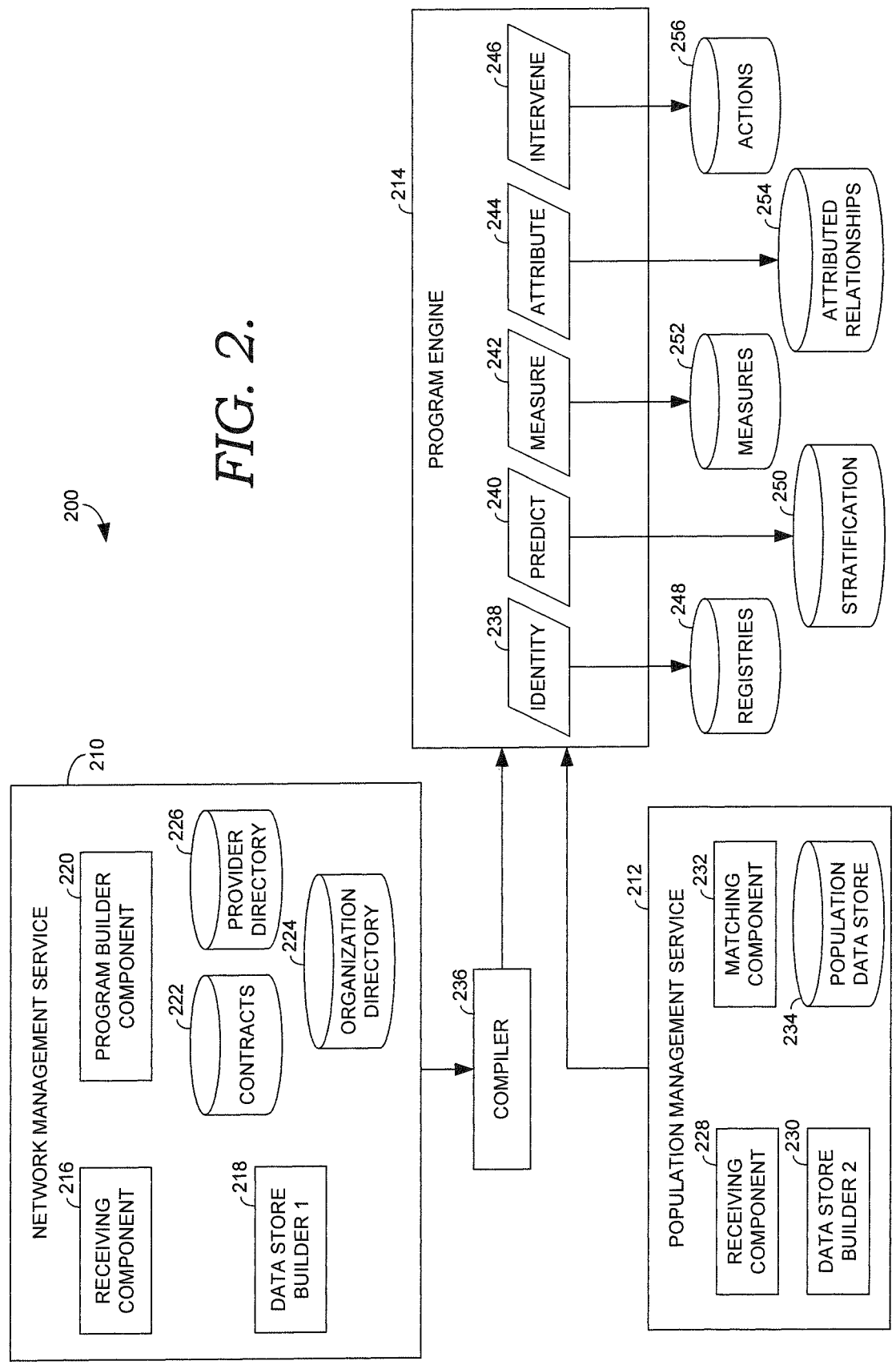
FIG. 2 is a block diagram of an exemplary system for managing population health suitable to implement embodiments of the present invention.

Turning now to FIG. 2, an exemplary population health management system 200 is depicted suitable for use in implementing embodiments of the present invention. The population health management system 200 is merely an example of one suitable computing system environment and is not intended to suggest any limitation as to the scope of use or functionality of embodiments of the present invention. Neither should the population health management system 200 be interpreted as having any dependency or requirement related to any single module/service/component or combination of modules/services/components illustrated therein.

The population health management system 200 includes a network management service 210, a population management service 212, a program engine 214 and a compiler 236 all in communication with each other through wired connections or through a network. The network may include, without limitation, one or more local area networks (LANs) and/or wide area networks (WANs). Such networking environments are commonplace in offices, enterprise-wide computer networks, intranets and the Internet. Accordingly, the network is not further described herein.

The network management service 210, the population management service 212, the program engine 214 and the compiler 236 are merely exemplary. While each of these components/services/modules is illustrated as a single unit, it will be appreciated that each of these components/services/modules is scalable. For example, the network management service 210 may in actuality include a plurality of computing devices in communication with one another. Components of the network management service 210, the population management service 212, the program engine 214 and the compiler 236 may include a processing unit, internal system memory, and a suitable system bus for coupling various system components, including one or more data stores for storing information (e.g., files and metadata associated therewith). Each of these components/services/modules typically includes, or has access to, a variety of computer-readable media.

In some embodiments, one or more of the illustrated components/services/modules may be implemented as stand-alone applications. In other embodiments, one or more of the illustrated components/services/modules may be integrated directly into the operating system of the population health management system 200. The component/services/modules illustrated in FIG. 2 are exemplary in nature and in number and should not be construed as limiting. Any number of components/services/modules may be employed to achieve the desired functionality within the scope of embodiments hereof. Further, component/services/modules may be located on any number of servers. By way of example only, the population health management system 200 might reside on a server, cluster of servers, or a computing device remote from one or more of the remaining components.

It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components/modules, and in any suitable combination and location. Various functions described herein as being performed by one or more entities may be carried out by hardware, firmware, and/or software. For instance, various functions may be carried out by a processor executing instructions stored in memory.

As shown in FIG. 2, the network management service 210 includes a receiving component 216, a data store builder 218, a program builder component 220 and various data stores 222, 224, and 226. The population management service 212 includes a receiving component 228, a data store builder 230, a matching component 232, and a population data store 234. In some embodiments, one or more of the components 216, 218, 220, 228, 230, and 232 may be implemented as stand-alone applications. In other embodiments, one or more of the components 216, 218, 220, 228, 230, and 232 may be integrated directly into the operating system of a computing device such as the remote computer 108 of FIG. 1. It will be understood that the components 216, 218, 220, 228, 230, and 232 illustrated in FIG. 2 are exemplary in nature and in number and should not be construed as limiting. Any number of components may be employed to achieve the desired functionality within the scope of embodiments hereof.

The data stores 222, 224, 226, and 234 are configured to store information used by network management service 210 and the population management service 212. The content and volume of such information in the data stores 222, 224, 226, and 234 are not intended to limit the scope of embodiments of the present invention in any way. Further, although each data store 222, 224, 226, and 234 is illustrated as a single, independent component, the data stores 222, 224, 226, and 234 may, in fact, be a plurality of storage devices, for instance, a database cluster, portions of which may reside on the network management service 210, the population management service 212, the program engine 214, and/or any combination thereof.

Turning first to the network management service 210, the receiving component 216 is configured to receive organizational data from one or more healthcare organizations. The healthcare organizations may bear some logical relationship to each other, or, alternatively, the healthcare organizations may be disparate with no logical relationship to one another. As used throughout this application, a healthcare organization may comprise a single healthcare facility with an associated group of healthcare providers such as physicians, pharmacists, nurses, health coaches, therapists, and the like. A healthcare organization may also comprise a network of healthcare facilities, each healthcare facility having an associated group of healthcare providers. The healthcare organization may create such networks in order to achieve certain financial and/or clinical objectives. The healthcare facilities may be located geographically close to one another or may be spread across a large geographical area. Further, the healthcare facilities may comprise a network of hospitals, clinics, provider offices, nursing homes, pharmacies, home health services, and the like. As such, the term "healthcare organization" as used herein is meant to be construed broadly to cover a wide range of healthcare scenarios.

The organizational data may include data about each healthcare facility such as operating hours, type of care provided, unique characteristics associated with the health care facility, geographic location, accessibility, associated providers, and the like. The organizational data may also include healthcare provider data such as names, credentials, affiliations, areas of practice, geographic location, provider preferences, current patient load, demographic characteristics such as gender or age, provider outcome data, and the like.

Continuing, the organizational data may also include contractual data. By way of background, when a healthcare organization enters into a payment agreement with a payer, a contract is generated that includes a variety of information or provisions. A payer refers to an entity that intends to pay or is responsible for payment of healthcare services. Payers include without limitation employers, government entities (such as Centers for Medicare and Medicaid Services), charities, patients, insurers and secondary insurers. The contract between a payer and a healthcare organization may include financial objectives (e.g., payment terms), clinical objectives, warranties, terms and conditions, and the like. For example, a payer may agree to pay a healthcare organization a certain amount if the healthcare organization meets certain quality measures or clinical objectives (e.g., a fee-sharing arrangement). The quality measures may include keeping readmission rates below a certain level, keeping costs of care low, meeting standards-of-care for certain disease conditions, and the like. As used in this application, the term "organizational data" is meant to be construed broadly to cover a wide range of information regarding healthcare organizations, healthcare providers, and contractual or agreement terms.

The data store builder 218 is configured to build, maintain, and update the data stores 222, 224, and 226 using information received by the receiving component 216. The contract data store 222 stores contractual information between one or more healthcare organizations and their associated payers; the contractual information, as mentioned, includes clinical objectives as well as financial objectives. The organization directory data store 224 stores organizational information pertaining to one or more healthcare organizations, and the provider directory data store 226 stores healthcare provider information. The information stored in the data stores 222, 224, and 226 may arise from disparate organizations or sources that bear no relationship to each other. The data stores 222, 224, and 226 may be networked storage or distributed storage including storage on servers located in the cloud. Thus, it is contemplated that for some embodiments, the information stored in the data stores 222, 224, and 226 is not stored in the same physical location. As new organizational information is received by the receiving component 216, the data store builder 218 updates the existing data stores 222, 224, and/or 226.

The program builder component 220 is configured to, in one aspect, automatically build one or more condition-specific or objective-specific program templates to be used by, for example, a healthcare organization to manage the health of a population segment or to achieve one or more objectives. In another aspect, a user, such as a programmer associated with a healthcare organization, can use the program builder component 220 to build a condition-specific or objective-specific program template that is customized to the particular healthcare organization. In general terms, a condition-specific or objective-specific program template may be defined as a systematic approach to identify, predict, and/or manage an objective or condition at a population, provider, or patient level. The program builder component 220 may have access to knowledge repositories that include algorithms, outcome-related goals, reference materials, standards-of-care, recommendation protocols, and the like. This information may be specific to a healthcare organization or facility, or the information may be promulgated by, for example, nationally-recognized medical organizations or governing bodies and be applicable to multiple different healthcare organizations.

As mentioned, in one aspect, the program templates may be condition specific and designed to better help healthcare organizations manage, for example, a population segment with a certain disease condition. The number and type of conditions are numerous and examples include wellness, heart disease, pre-diabetes, diabetes, stroke, and the like. The program templates are configured, in one aspect, to identify patients within a population segment who have a defined condition or have risk factors that may lead to the development of the condition. The program templates are also configured to stratify patients within the identified segment by degree of severity or risk or by disease type, and to generate interventions or action workflows designed to reduce disease severity or risk and to improve outcome. Additional uses for the condition-specific program templates are to measure outcomes related to treatment interventions, predict outcomes based on the implementation of a proposed action, and also to attribute patients within the identified segment to appropriate care providers (e.g., primary care physicians, health coaches, specialists such as endocrinologists, podiatrists, and the like) best suited to treat the condition in a cost-effective manner.

Program templates may also be objective-specific and designed to assist a healthcare organization reach a defined objective. Objective-specific templates include public health surveillance, contract management, organization management, provider incentives, research solutions, interoperability solutions, creation of research data marts, patient outreach, and the like.

As mentioned, the condition-specific and/or objective-specific program templates may be automatically generated, or may be automatically generated and modified by a user, or may be built entirely by the user. The user in this case, may include a programmer or administrative personnel associated with a healthcare organization. This user may customize the template so that it more directly reflects the characteristics of the organization including any contractual provisions that the organization adheres to. For instance, the user may modify or customize the template by modifying population qualifiers, reference ranges, measurement thresholds, intervention strategies, algorithms, nomenclature concepts, and the like.

Figure 5:
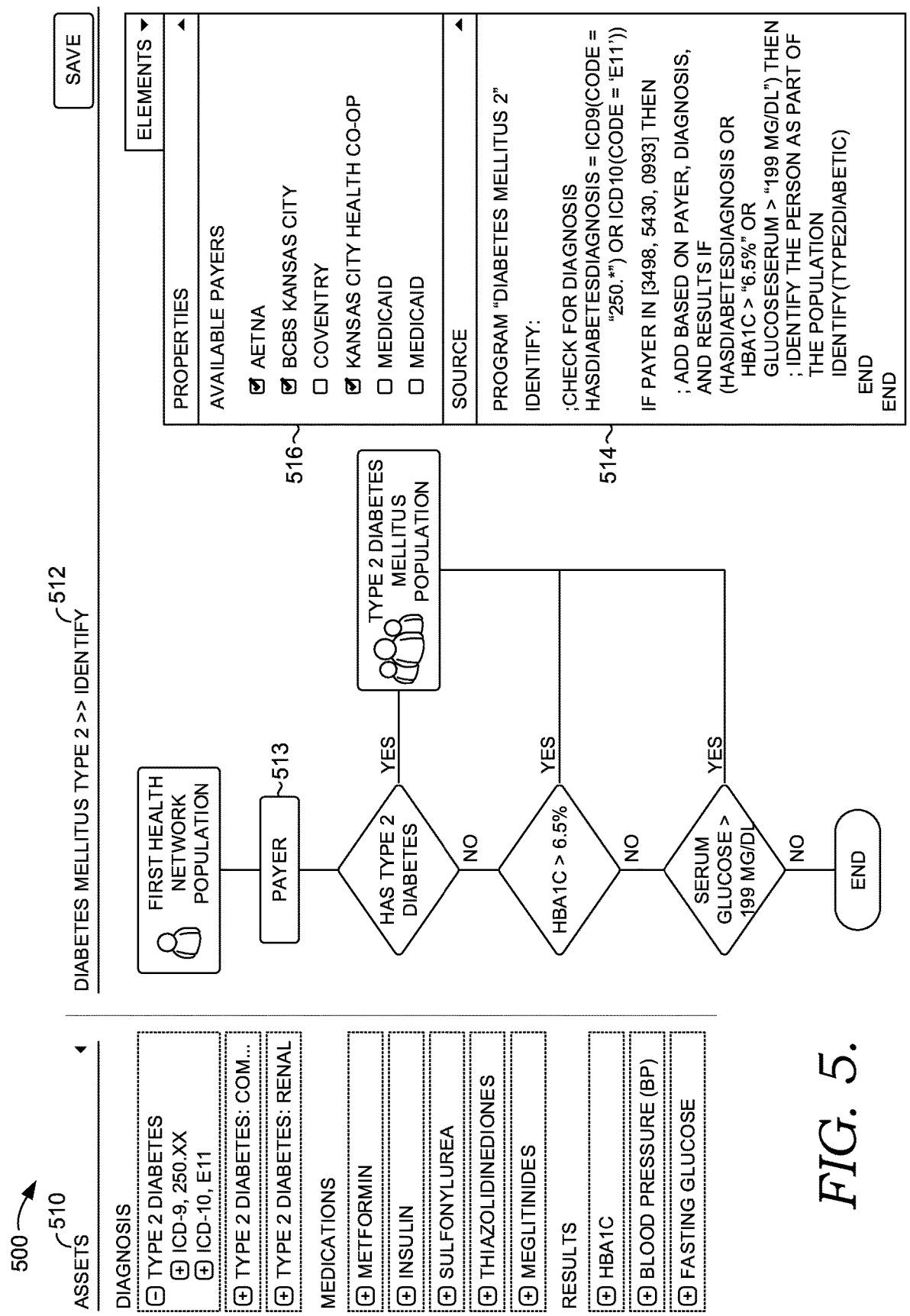
FIG. 5 is an exemplary graphical user interface suitable to build a condition-specific or objective-specific program template in accordance with an embodiment of the present invention.

FIG. 5 depicts an exemplary graphical user interface (GUI) 500 of a logic editor that may be used to modify and/or build a condition-specific program template. The GUI 500 includes a clinical asset library area 510. In this case, the clinical asset library area 510 includes clinical assets or concepts associated with the disease condition diabetes mellitus. Assets may include diagnoses (including diagnostic codes), medications, lab values, and the like. The GUI also includes a template building area 512. In this case, a program template used to identify patients in a population who have diabetes or are at risk of developing diabetes is being generated. The GUI further includes a source code area 514 where source code is automatically generated and displayed as the program template is being built in the template building area 512. The source code area 514 is configured to enable a user to make changes directly to the source code; these changes are automatically reflected in the template building area 512. In one aspect, the source code is specific to population health management. Additionally, the GUI 500 includes area 516 which, in this case, is initiated when the user selects "Payer" 513. The area 516 presents a list of payers, and the user is able to select payers that are associated with the healthcare organization.

Turning back to FIG. 2 and moving on the population management service 212, the receiving component 228 is configured to receive patient data from one or more sources that may be disparate in nature. Patient data, as used herein, refers to any type of data, including healthcare or medical care data that is related or relevant to a patient. Patient data may include, but is not limited to, clinical data, financial data, and activity data.

Clinical data, as used herein, refers to any healthcare or medical data particular to a patient. In embodiments, clinical data is medical care or healthcare data resulting from or associated with a health or medical service performed in association with a provider in a healthcare environment (e.g., lab test, clinical encounter, eCare, eVisit, etc.). Clinical data may include, but is not limited to, a health history of a patient, patient information, patient identifiers, patient demographics (e.g., age, gender, race, etc.), diagnoses, treatments, a family history, genomic history, immunization records, medications, test results, allergies, adverse reactions, procedures performed, social history, advanced directives, alerts, claims data, vital sign information, data traditionally captured at the point of care or during the care process, a combination thereof, and the like. The clinical data may be derived from claims data, data supplied by the patient's insurer, electronic medical record data, device data, health information exchange (HIE) data, personal health records (PHRs), continuity-of-care documents (CCD), patient-inputted data (via, for example, a patient portal), provider-inputted data, pharmacy data, and the like.

Financial data refers to any financial information relevant to a patient, such as insurance data, claims data, payer data, patient-provided data, and the like. For example, a patient may input via a patient portal financial information such as income, purchasing habits, credit card information, etc. Activity data refers to data that may impact a patient's health but is derived from sources outside of or remote from the patient's healthcare environment. For example, activity data may comprise data supplied by county health agencies, state health agencies, communities, research data marts, federal public health agencies, and the like. Representative types of activity data include disease statistics or crime statistics associated with a community or geographic area, socioeconomic characteristics of population segments located in a particular geographic area as indicated by zip code (e.g., age, income level, education level, race, gender, and the like), support services provided by a community such as elder care programs, health education programs, health clinics, church programs, nutrition-assist programs, exercise programs, and the like.

The data store builder 230 is configured to build, maintain, and/or update the population data store 234 using the patient data received by the receiving component 228. The data store builder 230 receives the incoming raw data in various formats or nomenclature including proprietary formats. The raw data may include data that is structured, unstructured or semi-structured. A copy of all the raw data received by the data store builder 230 is stored in its raw form. This enables the population health management system 200 to derive new knowledge using the raw data at a later point in time.

For each source of data, the data store builder 230 transforms the raw data into industry-standard nomenclatures such as Logical Observation Identifiers Names and Codes (LOINC), Unified Medical Language System (UMLS), or Systemized Nomenclature of Medicine (SNOMED), and compiles the data by source into a reference record. Reference records are cleansed, standardized, and machine-readable. The reference records support all industry-standard terminologies, which enables the fidelity of the data sources to be retained. When the raw data is in a proprietary format, the data store builder 230 leverages machine learning techniques to map codes to industry-standard terminologies. Machine learning techniques recommend appropriate standard terminology codes thus speeding up the mapping process. The data store builder 230 is also configured to apply natural language processing techniques to data contained in clinical notes, reports, and documents. The data store builder 230 is configured to reconcile conflicting pieces of data or synthesize pieces of data that should be viewed together and to learn from each data source thereby enabling the mapping and transformation processing times to be reduced for new data sources.

As mentioned, the data store builder 230 is configured to track the source of the data and associate the source with the source's reference record. The reference record for a particular data source contains consent, access, and/or privacy rules associated with the data source. A particular reference record may be utilized by multiple different organizations. This is especially useful in situations where the organizations that utilize a particular reference record change over time. By way of illustrative example, a provider group may provide data to the population health management system 200. The provider group may initially be affiliated with a first healthcare organization and grant the first healthcare organization access rights to the provider group's reference record. At some later point in time, the provider group may cancel its contract with the first healthcare organization and establish a contract with a second healthcare organization. In this case, instead of the provider group having to re-send all of its data to the second healthcare organization, it can simply grant the second healthcare organization access rights to its reference record and withdraw access rights from the first healthcare organization.

The data store builder 230 combines the information contained in the different reference records to form person-centric longitudinal health records known as population records. Each record is longitudinal in that it contains information on all of the patient's health encounters even though the encounters may have occurred at disparate locations and with disparate providers. Each population record is stored in the population data store 234. Thus, the population data store 324 includes multiple population records relevant to a population of patients. The data store builder 230 utilizes the matching component 232 to match patients with their data and create the person-centric longitudinal population records.

The matching component 232 utilizes one or more probabilistic patient matching algorithms to match patients to their clinical, financial, and activity data. Patients may be matched to their data based on for example, patient name, patient identifiers, and the like. For more general data such as socioeconomic conditions by zip code, a patient may be matched to an appropriate set of socioeconomic data using, for example, the patient's zip code. The matching component 232 is also configured to reconcile all of the patient's records even if the records are associated with different patient identifiers. For instance, a pharmacy may use a first patient identifier when dispensing medications to a patient while a care clinic may use a second patient identifier when treating the patient. The matching component 232 is configured to reconcile these patient identifiers and match all of the pertinent medical information associated with the patient. Each patient's data is also normalized via grouping codes from multiple terminologies that mean the same thing thereby reducing redundant data.

Different patient matching algorithms may be utilized by the matching component 232 to generate different population records suitable for different purposes or use cases. For example, one algorithm may be used to create a population record that includes identified, detailed clinical information about the patient. This type of population record is suitable for use by clinical-type programs that need access to granular data about the patient. A different matching algorithm may be used to create a population record that is de-identified (e.g., stripped of patient-identifying data). A de-identified population record may contain less granular information about the patient and be suitable for use by research-type programs after obtaining the patient's consent. Other patient-centric population records may be created for, for instance, analytics purposes.

The population data store 234 may be networked storage or distributed storage including storage on servers located in the cloud. Thus, it is contemplated that for some embodiments, the information stored in the population data store 324 is not stored in the same physical location. The information within the population data store 234 may exist in a variety of standardized formats including, for example, narratives and other data.

Figure 7:
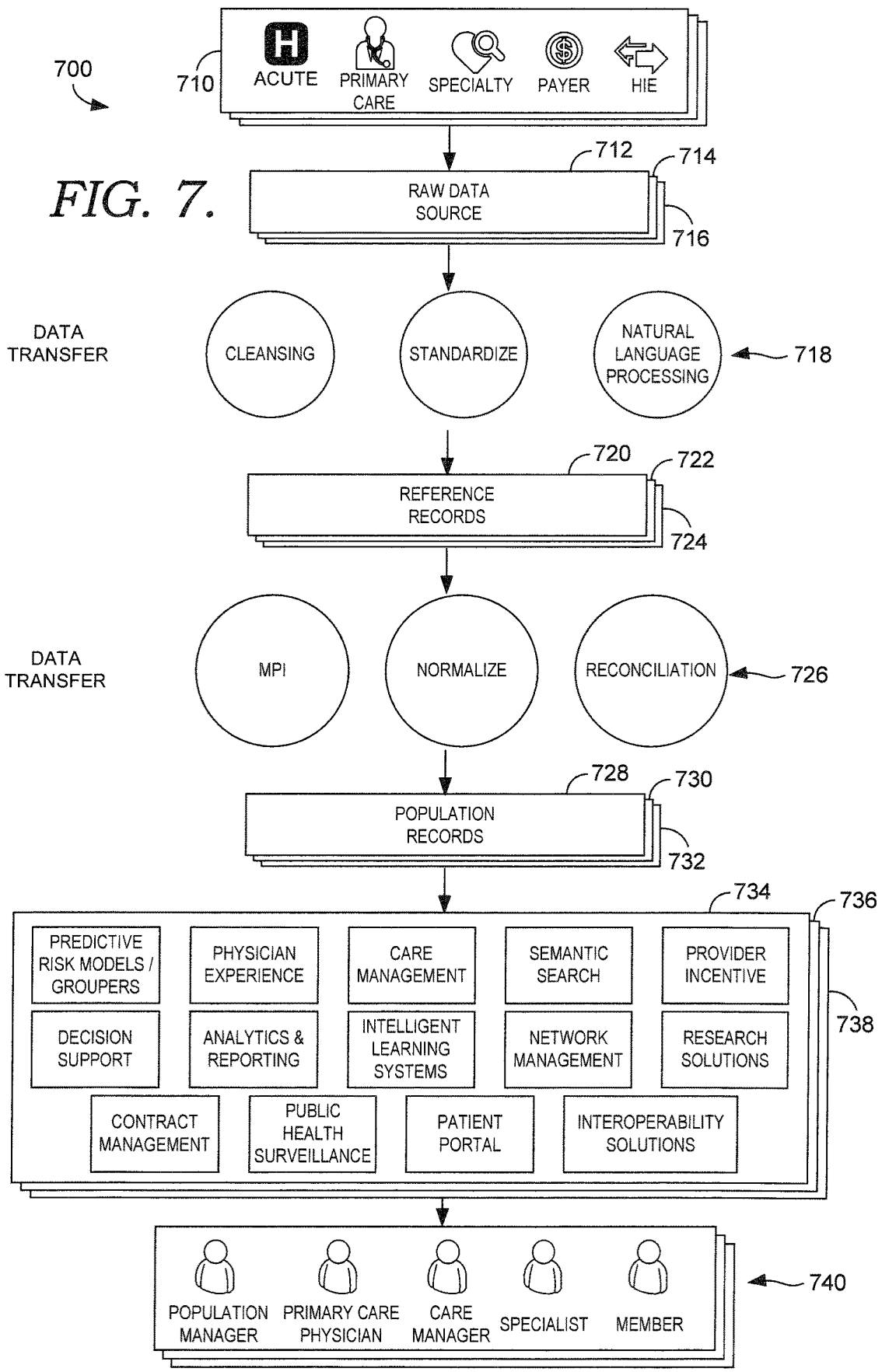
FIG. 7 is a schematic illustration of relationships between raw data sources, reference records, and population records in accordance with an embodiment of the present invention.

FIG. 7 depicts the relationship between the raw data, reference records, and population records and is referenced generally by the numeral 700. Raw data sources 710 include such sources as acute care facilities, primary care providers, specialty providers, payers, HIE, pharmacies, patient-inputted information, public health agencies, community sources, and the like. Additional data sources beyond those shown are contemplated. The raw data sources 710 may contribute data in a variety of nomenclatures and formats, including proprietary formats. The raw data received from the raw data sources 710 is stored by source in raw data stores 712, 714, and 716. The raw data stores 712, 714, and 716 may be networked storage or distributed storage including storage on servers located in the cloud.

At a step 718, the raw data is transformed into industry-standard nomenclatures by, for example, techniques such as cleaning, standardizing, natural language processing, machine learning, and the like. After transformation at step 718, the transformed data is stored in reference records 720, 722, and 725. Each reference record 720, 722, or 724 stores transformed data from a single data source. The reference records 720, 722, and 722 may be networked storage or distributed storage including storage on servers located in the cloud.

At a step 726, the data from the reference records 720, 722, and 714 is combined and undergoes a second transformation process before being stored in patient-centric population records 728, 730, and 732. The transformation process at step 726 includes application of probabilistic patient matching algorithms, normalization, and reconciliation as explained above. The population records 728, 730, and 732 may be networked storage or distributed storage including storage on servers located in the cloud.

Different programs 734, 736, and 738 can access the population records 728, 730, and 732 or sub-portions of the population records 728, 730, and 732. The programs may be condition-specific such as decision support, patient registries, care management, predictive risk, and the like. Likewise, the programs may be objective-specific such as public health surveillance, interoperability solutions, attribution, outreach, intelligent learning systems, contract management, provider incentive, physician experience/outcome, network management, and the like. A particular population record may be accessed by more than one program. Likewise, a particular program may access a plurality of population records.

At a step 740, different end-users are able to utilize the output of the programs 734, 736, and/or 738 via one or more computer applications. End-users are numerous but representative examples include population managers, primary care physicians, care managers or health coaches, specialists, patients, healthcare organization administrators, payers, and the like.

Turning back to FIG. 2, the compiler 236 is configured to extract one or more condition-specific or objective-specific program templates from the network management service 210 and use information in the contracts data store 222, the organization directory data store 224, and the provider directory data store 226 to modify or localize the template to a particular healthcare organization. This may be done in response to the particular healthcare organization initiating and/or updating a population health management program directed to the disease condition or an objective that is the subject of the program template. After modifying the condition-specific program template using the organizational data, the compiler 236 outputs one or more software agents or programs that may be used by, for example, the program engine 214.

The program engine 214 is configured, at run-time, to access patient population data stored in population records in the population data store 234 and execute the customized condition-specific or objective-specific programs against one or more of the population records, or sub-portions of the population records to generate patient population data for the healthcare organization.

The program templates may include identification programs 238 that identify different types of population segments. For example, population segments may be identified based on a condition such as, for example, wellness, diabetes, stroke, hypertension, and the like. Population segments may be identified based on affiliation with a particular healthcare organization or a particular provider. Additionally, population segments may be identified that have a condition and are eligible for different outreach programs. The type of identification is dependent upon the underlying purpose of the program. The identified segment along with associated patient data is stored in a registry 248 and is available for use by various applications utilized by the healthcare organization.

Another program is a prediction program 240 that takes a population segment identified by the identification program 238 and stratifies patients within the segment based on disease type, and/or severity of the disease condition, and/or severity of risk for contracting the disease condition. For example, a diabetes population may be identified and then stratified based on whether the patient has Type 1 Diabetes versus Type 2 Diabetes, whether the diabetes is controlled versus uncontrolled, and/or whether the patient(s) is compliant with medication versus non-compliant. Other stratification schemes may be employed such as stratifying by cost of care, demographic features, and the like. The stratification information is stored in a stratification data store 250 that is available for use by various applications utilized by the healthcare organization.

Figure 8:
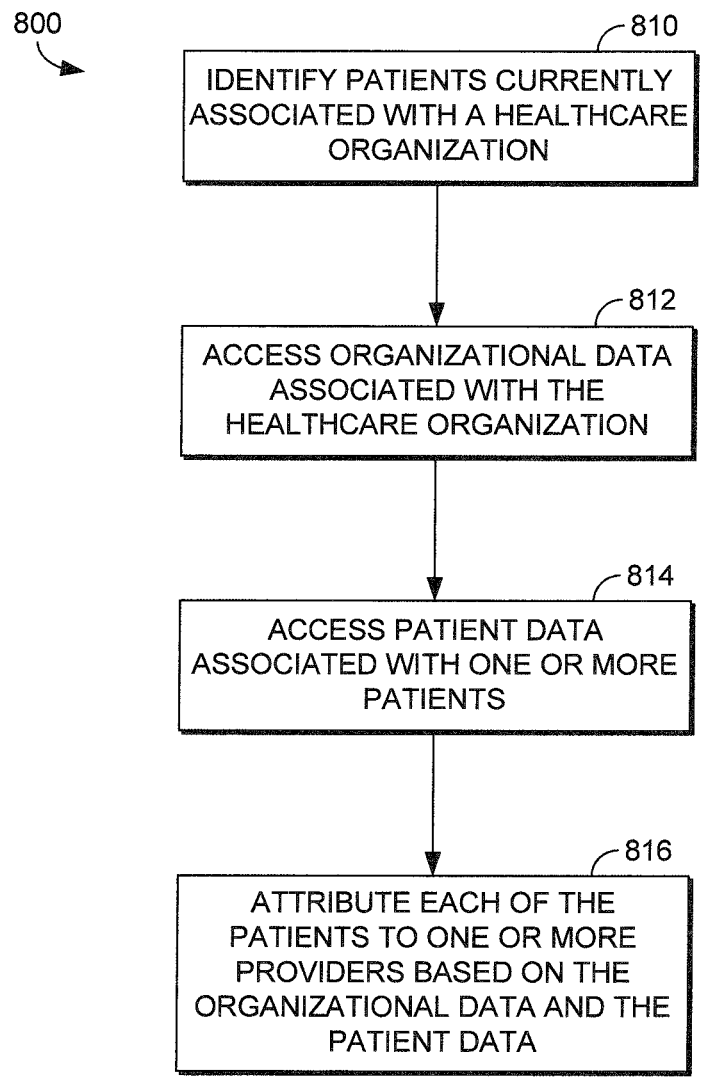
FIG. 8 is a flow diagram of an exemplary method of attributing patients to one or more providers in accordance with an embodiment of the present invention.

Yet another program is an attribution program 244 that attributes patients to various healthcare providers within a healthcare organization. Attribution is geared towards pairing a patient with an optimal set of healthcare providers to effectively manage the patient while keeping costs down. As explained above, the attribution program may be customized to the healthcare organization or may be a standard attribution program. Turning now to FIG. 8, FIG. 8 depicts a flow diagram of an exemplary method 800 of attributing patients to one or more healthcare providers associated with the healthcare organization. At a step 810, a program engine, such as the program engine 214 of FIG. 2, that is running an attribution program for the healthcare organization accesses population records (such as the population records 728, 730, and 732 of FIG. 7) to identify patients that are presently affiliated with the healthcare organization.

At a step 812, organizational data associated with the healthcare organization is accessed. The organizational data may be stored in association with a data store such as the contracts directory 222, the organization directory 224, and the provider directory 226 of FIG. 2. The organizational data is searched for "supply" data such as identity and number of providers associated with the organization, current workloads associated with the providers, identification of providers by specialty, location information of the providers including whether the provider is accessible to people with disabilities, outcomes (e.g., scores) associated with different providers, and the like.

The organizational data also includes objectives specified in one or more payer contracts that the healthcare organization has entered into. The objectives specified in the payer contracts may indicate that providers meet quality measures for a predefined number of patients (these patients are known as "scorable patients") before the provider and/or the organization is reimbursed and/or receives incentive fees from the payer. If the attribution program is a standard program that is currently not customized to the healthcare organization, organization-specific parameters may be accessed. These parameters specify attribution rules for the healthcare organization. For example, the healthcare organization may have a rule specifying that patients with low levels of complexity be assigned solely to a primary care physician, while patients with high levels of complexity be assigned to a primary care physician as well as a specialist.

At a step 814, the program engine again accesses the population records of those patients identified as being affiliated with the healthcare organization to determine, among other things, previous and current provider relationships associated with the patients. This is possible because each population record is longitudinal in nature and contains a history of all healthcare encounters associated with the patient, even if the encounters occurred at disparate locations and disparate times. Other examples of patient information that is accessed include geographic location of the patient, disease conditions, personal preferences regarding the type of provider the patient wishes to see (e.g., female versus male, board certified, older versus younger, specialist versus primary care, and the like), socioeconomic information as determined by, for example, the zip code at which the patient resides, demographic information (e.g., gender, age, and the like), financial information as determined by claims data or patient-provided data, genomic information associated with the patient (e.g., whether the patient has been identified as having a gene mutation leading to an increased risk of cancer or disease), and whether the patient is disabled and requires specialized access to provider offices. Patient data may also include social information such as the presence of family care givers, alcohol and tobacco use, church affiliations, use of support services, and the like. Some of this information may be supplied directly by the patient through a patient portal while other information is gleaned from different data sources as explained above.

At a step 816, the program engine attributes each of the patients associated with the healthcare organization to one or more providers within the healthcare organization based on both the organizational data and the patient data. The program engine is designed to take into account each piece of organizational data and patient data when defining the attribution scheme with the result that the attribution scheme is not only customized to the healthcare organization but is personalized to the patient. For example, a first healthcare organization may utilize health coaches while a second healthcare organization does not. An attribution scheme for the first healthcare organization would include health coaches while an attribution scheme for the second healthcare organization would not include health coaches.

In one aspect, a tiered attribution scheme may be utilized wherein a patient is first attributed to a certain type of provider based on the organizational data, and then the actual identity of the provider is determined based on patient data. For example, a diabetic patient may first be attributed to a primary care physician and an endocrinologist based on organization-specific parameters or rules. Patient data is then used to determine, for example, a primary care physician and an endocrinologist within geographic proximity to the patient and who meet patient preference factors. The output of the attribution program is stored in association with an attributed relationships data store such as the attributed relationships data store 254 of FIG. 2. This data store can also be utilized by various applications.

In one aspect, an existing attribution scheme can be modified by providers. In this aspect, the provider may be presented with a list of patients that have been attributed to him or her. The provider has the option to accept and/or reject the attribution scheme. If accepted, the attribution scheme is implemented. If the provider chooses to reject the attribution scheme, the provider is given the option of proposing a new attribution scheme. For example, in an intra-office setting, the provider may suggest that a patient be attributed to another provider within the group. Based on the proposal, a segment of the attribution program may be re-executed to determine if the proposed change is feasible based on organizational and patient data. In another aspect, a healthcare organization is able to run an attribution scenario using organizational data to see if the attribution scenario is feasible before actually implementing the attribution scenario.

Figure 9:
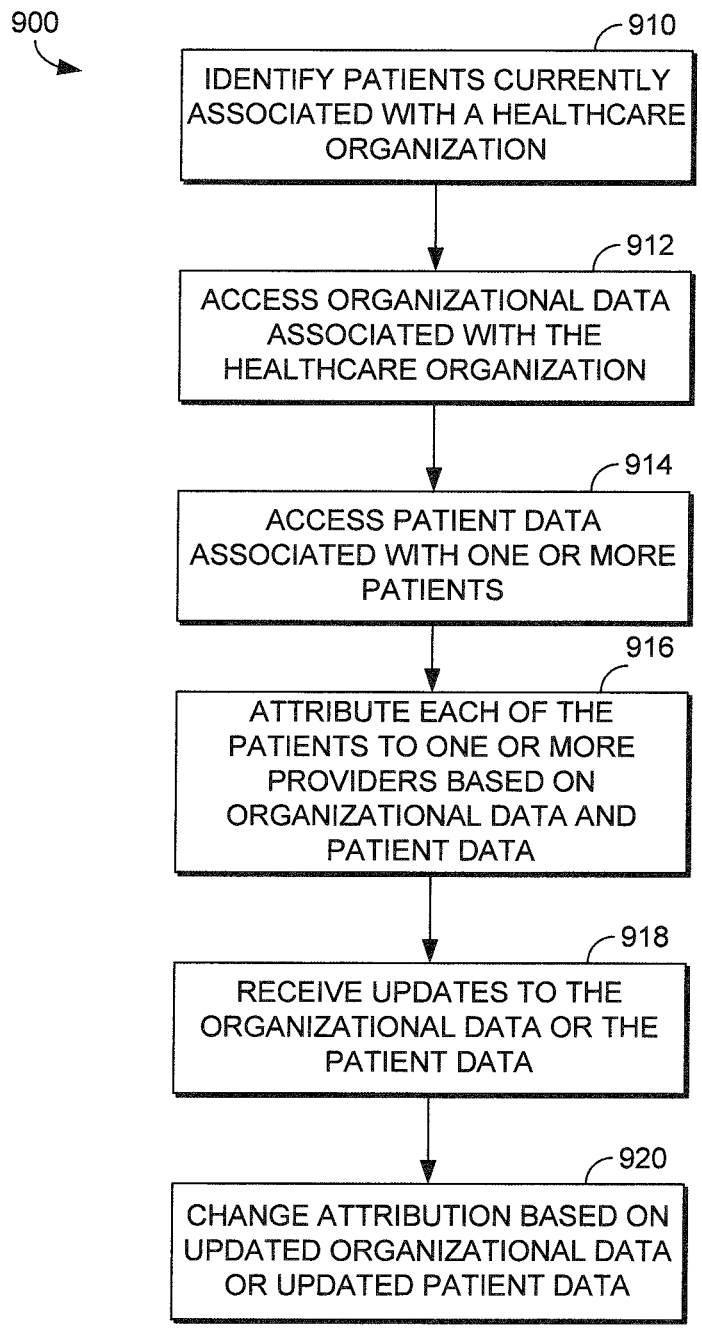
FIG. 9 is a flow diagram of an exemplary method of modifying an attribution scheme based on updated organizational or patient data in accordance with an embodiment of the present invention.

FIG. 9 depicts another flow diagram of an exemplary method 900 of updating an attribution scheme based on the receipt of new organizational or patient data. At a step 910, population records are accessed by an attribution program engine to determine patients who are currently associated with a healthcare organization. At a step 910, organizational data associated with the healthcare organization is accessed to determine the number and identity of providers associated with the organization, location of the providers, providers by specialty, outcomes associated with the providers, and the like. As explained above, the organizational data may also include objectives specified in payer contracts as well as organization-specific rules or parameters regarding attribution.

At a step 914, the population records of those patients who are currently affiliated with the healthcare organization are again accessed to determine patient information such as previous provider relationships, current provider relationships, patient preferences, social history, and the like. At a step 916, each of the patients is attributed to one or more providers based on the organizational data and the patient data.

At a step 918, updates to one or both of the organizational data and/or the patient data are received. The types of updates may include any change to the organizational data and/or the patient data such as the addition of a new patient to the network, changes in patient or provider location, updated patient preferences, change in patient disease state that may necessitate the addition of another provider to care for the patient or the deletion of a currently-attributed provider, the addition or deletion of providers associated with the healthcare organization, a modification to a payer contract that changes incentive or reimbursement objectives, new organization attribution rules, and the like.

In response to the updated organizational and/or patient data, the attribution scheme may be automatically modified at a step 920. Like above, the modification is made based on both the organizational data and the patient data. By way of illustrative example, updated organizational data may indicate that a provider has moved his/her office location. A patient currently attributed to the provider may initially be attributed to another provider that is located closer to the patient. However, this patient's preferences may indicate that the patient wishes to maintain the relationship with the current provider regardless of the provider's location. In another case, a patient may indicate that geographic location of the provider is his/her primary concern and, thus, this patient would be attributed to another provider that is located closer to the patient.

Figure 10:
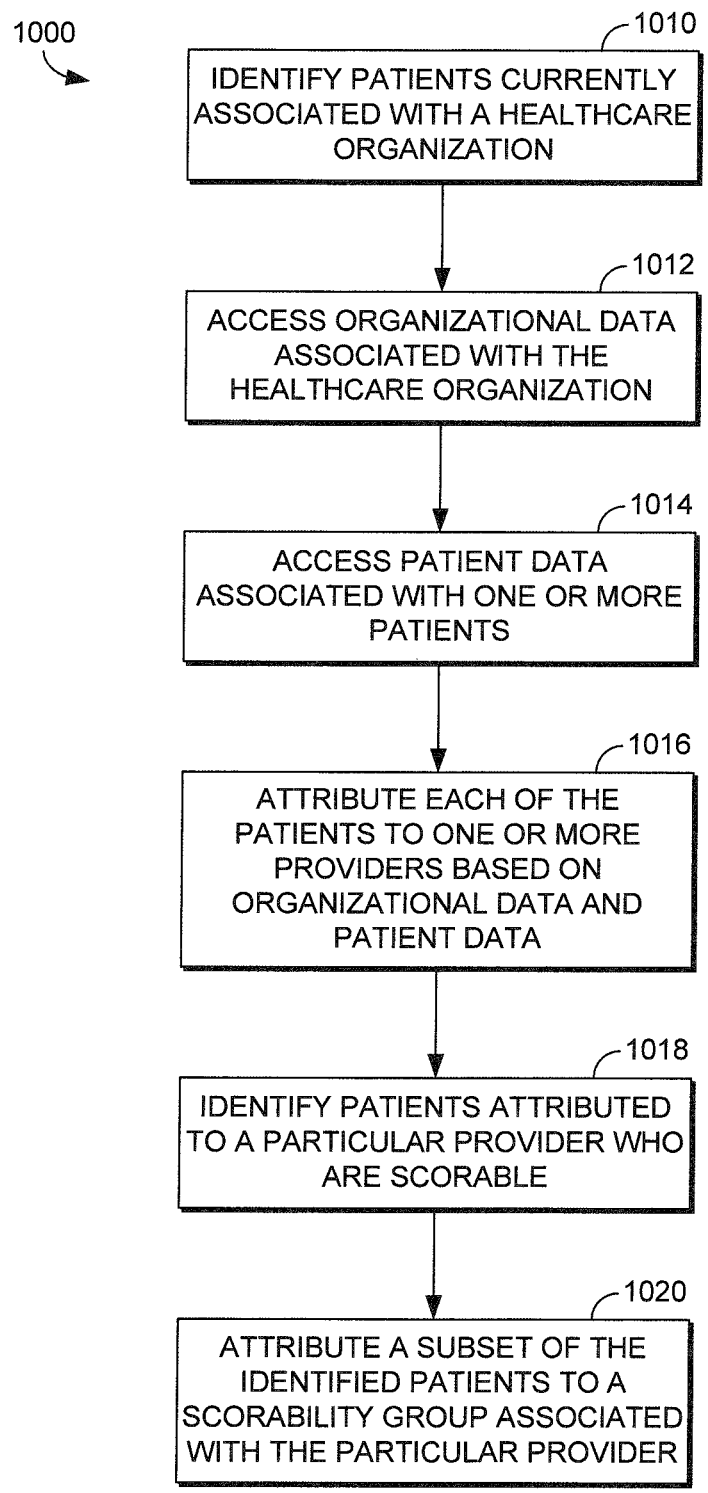
FIG. 10 is a flow diagram of an exemplary method of attributing patients to scorable patient groups in accordance with an embodiment of the present invention.

FIG. 10 depicts a flow diagram of an exemplary method 1000 of attributing scorable patients to a provider. As briefly outlined above, the concept of a "scorable patient" is based on new payer strategies for reimbursing and/or incentivizing providers and healthcare organizations to provide quality care at a reasonable cost. One strategy that is used by Medicare is to base reimbursement off of re-admission rates of patients who suffer from certain disease conditions such as, for example, pneumonia. If readmission rates for these patients are kept below a contract-specified threshold, reimbursement at full levels is provided to the organization and/or provider. Many private payers are instituting fee-sharing or incentive arrangements with healthcare organizations. These arrangements provide financial incentives to healthcare organizations and providers if certain quality measures or objectives are met. For instance, a provider caring for diabetic patients may receive an incentive if a certain number of his diabetic patients maintain their hemoglobin A1C levels below a defined threshold. The quality measures and/or objectives associated with scoring are embodied in payer contracts which are part of the organizational data associated with the healthcare organization. Those patients who are part of the group of patients for whom quality measures are being monitored and upon which incentives are based are considered a scorable patient group.

With this as a background, and turning to FIG. 10, at a step 1010, patients currently associated with a healthcare organization are identified by accessing the patient-centric longitudinal population records. At a step 1012, organizational data associated with the healthcare organization is accessed. Among other things, the organizational data includes contract objectives specifying quality measures to be met by providers and/or the organization including the number of patients that should be in the scorable patient groups.

At a step 1014, population records of those patients currently associated with the healthcare organization are accessed and pertinent patient data related to attribution is identified. At a step 1016, each of the patients is attributed to one or more providers based on both the organizational data and the patient data as outlined above.

At a step 1018, and with respect to at least one of the providers, patients attributed to the provider who are scorable are identified. Again, this may be based on information contained in the population records and on contract data. A patient is identified as scorable if he or she meets the parameters spelled out in the payer contract. For instance, a payer contract may specify that a patient is scorable for diabetes management if the patient is between a certain age range and suffers from Type 1 diabetes. Patients meeting these criteria who have been attributed to the provider are thus identified as scorable.

At a step 1020, a subset of the scorable patients is attributed to the provider as a scorable patient group. Again, this may be based on terms in the payer contract that specify how many patients should be in a scorable group in order to measure achievement of quality measures. Thus, for example, although a provider may be attributed 1000 patients, only 200 of these may be considered scorable, and of these, only 60 are placed in the measured scorable group.

Yet another program is a contract and organization management program (not shown in FIG. 2) used by healthcare organizations to manage financial and clinical objectives between payers, providers, and patients. As explained above, a healthcare organization's organizational data includes contract data, data about the healthcare organization, and provider data. As contracts are established between the healthcare organization and payers, or between the healthcare organization and its providers, the contracts are digitized and stored in association with, for example, the contracts data store 222. The contracts contain contract objectives defining terms under which reimbursements are made and/or incentives provided to the healthcare organization and/or its providers. Some of these contract objectives include quality measure contract objectives. Each quality measure contract objective describes a quality measure to be met, the number of patients to be included in the quality measure group (i.e., the scorable patient group), and the percentage or number of patients in the scorable patient group that are required meet the quality measure before an incentive is provided. For instance, a quality measure contract objective for a provider associated with the healthcare organization may specify that an incentive of a defined amount will be awarded if 60% of a 60 patient scorable group attributed to provider have hemoglobin A1C levels below a predefined threshold. The amount of the incentive may be scaled based on the percentage met. Quality measure contract objectives defined at the organization level may provide incentives to the organization if, for example, a certain percentage of its providers meet quality measure contract objectives for one or more conditions.

Figure 11:
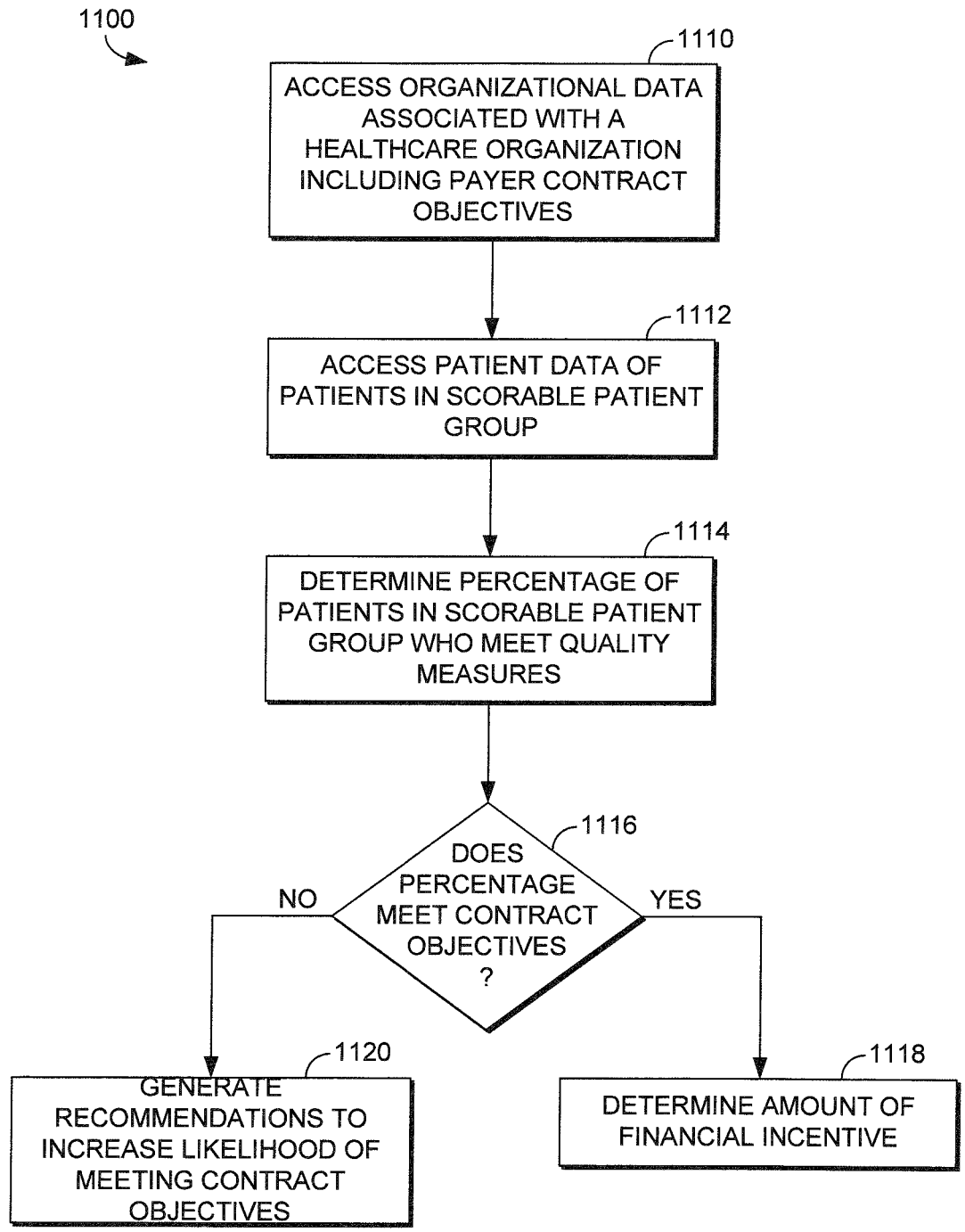
FIG. 11 is a flow diagram of an exemplary method of a healthcare organization managing contracts in accordance with an embodiment of the present invention.

With this as a background, and turning to FIG. 11, a flow diagram is depicted of an exemplary method 1100 of a healthcare organization managing its contracts using organizational data and patient data stored in population records. At a step 1110, organizational data associated with the healthcare organization is accessed from, for example, the contracts data store 222, the organization directory 224, and the provider directory 226 of FIG. 2. The organizational data may include, among other things, current and historical provider outcome data, current and historical organization outcome data, current and historical attribution schemes including current scorable patient groups, department or provider utilization data (e.g., radiology utilization, emergency room utilization, and the like), and the like. The organizational data further includes contract data such as contract objectives associated with quality measures. The contracts may be between payers and the healthcare organization, between the organization and its providers, and/or between payers and providers associated with the healthcare organization. The quality measure contract objectives may be set at both the provider level and the organization level. After being accessed, the organizational data may be further stratified based on, for example, payer, provider, scorable patient groups, and/or quality measures.

At a step 1112, patient data of patients in the scorable patient groups is accessed from population records stored in association with, for example, the population data store 234. The patient data accessed includes data related to the quality measure contract objectives. The type of data accessed is dependent on the nature of the quality measure but may include lab results, procedure results, diagnoses, indications of whether actions have been taken or attempted to be taken, readmission rates, and the like. After being accessed the patient data may also be stratified based on, for example, scorable patient group, payer, attribution to a particular provider, and the like.

At a step 1114, for each identified scorable patient group, it is determined the number of or the percentage of patients in the scorable patient group who meet the quality measure (s) as specified by the quality measure contract objectives. At a step 1116, a determination is made for each scorable patient group whether the percentage of patients in the scorable group that meet the respective quality measure is equal to or greater than the percentage or number set forth in the quality measure contract objective. Additionally, a determination may be made of the percentage or number of providers associated with the healthcare organization whose patients meet the quality measure contract objectives.

If, at a step 1118, it is determined that the percentage is equal to or greater than that set forth in the quality measure contract objectives, then an amount of financial incentive is determined. Again, the amount of the incentive is dictated by the contract terms and may be scaled based on the percentage met. The amount of financial incentive may be determined at the provider level and the organization level.

If, however, at a step 1120, it is determined that the percentage is less than that specified in the quality measure contract objectives, then one or more recommendations are automatically generated that will enable the healthcare organization to better meet the contract objectives. The recommendations may include changing the current attribution scheme to re-align poor performing patients with providers that have historically better provider outcomes, changing the current attribution scheme to address the over- or under-utilization of providers or departments (a concept known as venue shifting), making recommendations on types of providers that should be hired to better assist patients in meeting quality measures, and the like. By way of illustrative example, outcome data may indicate that providers in the organization's emergency room department are not meeting quality measure contract objectives because the department is being over utilized. Based on the type of quality measures not being met, a recommendation may be generated suggesting that, for example, a health coach and a primary care physician be hired by the organization. Recommendations may also be made as to which quality measures need most improvement so that the healthcare organization may make appropriate changes including, for example, increasing efforts at patient outreach. Besides generating recommendations at step 1120 if contract objectives are not met, the financial impact of not meeting those contract objectives may also be determined. This may be broken down by provider, provider groups, provider type, payers, type of quality measures, and the like.

Besides the method outlined in FIG. 11, the contract and organization management program may also utilize organizational and patient data to generate information relating to the achievement of quality measures. This type of information may include a summary of performance-to-date, projections regarding future performance, high-performing providers versus low-performing providers, high and low performing specialties, high and low performing provider groups, high and low performing quality measures, payer performance, cost effectiveness of providers and/or payers, and the like. All of the information generated by the contract and organization management program is stored in a data store that is available for use by the healthcare organization via one or more computer applications.

Figure 12:
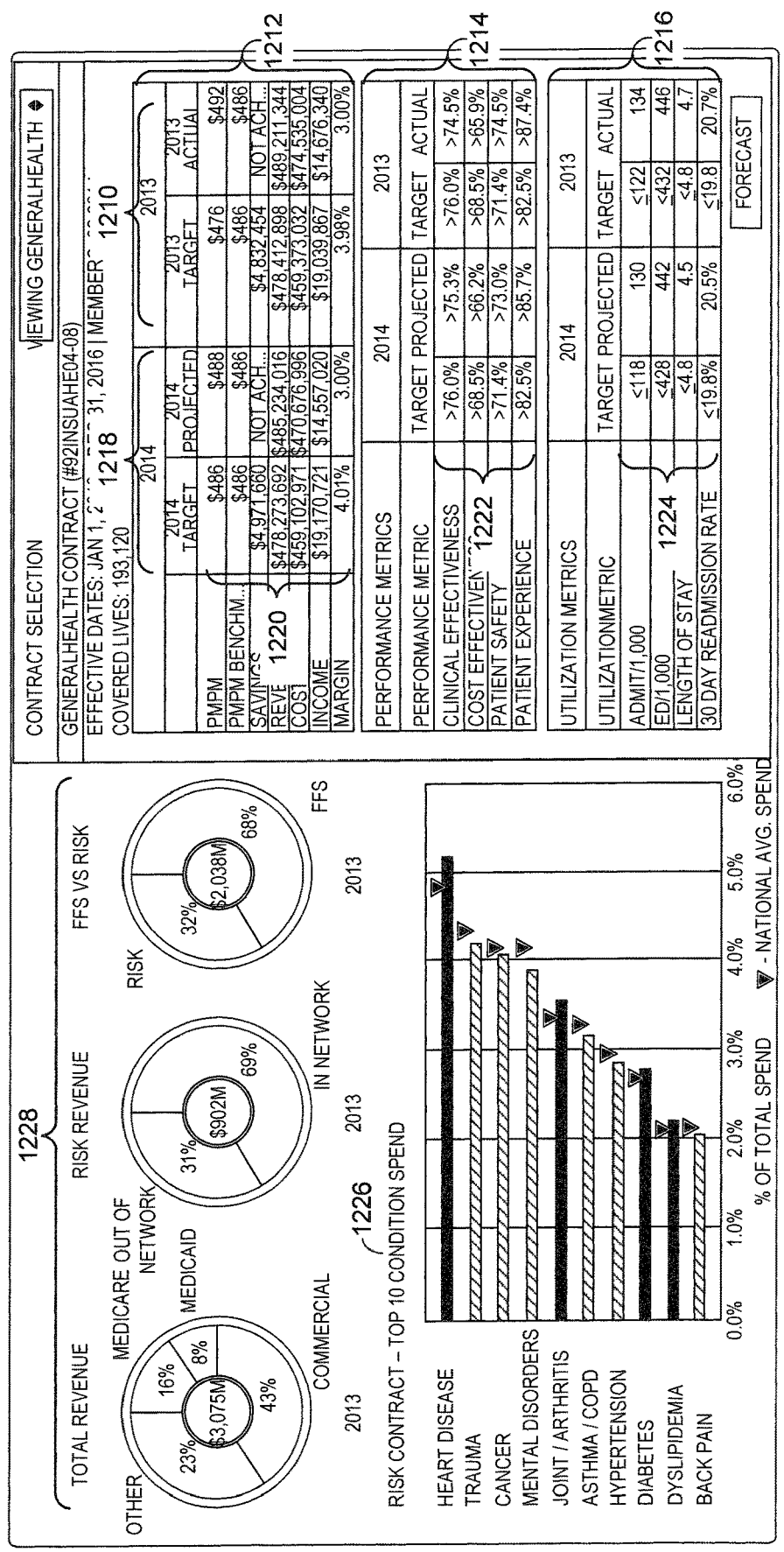
FIG. 12 is an exemplary graphical user interface for presenting data related to current contract performance in accordance with an embodiment of the present invention.
Figure 13:
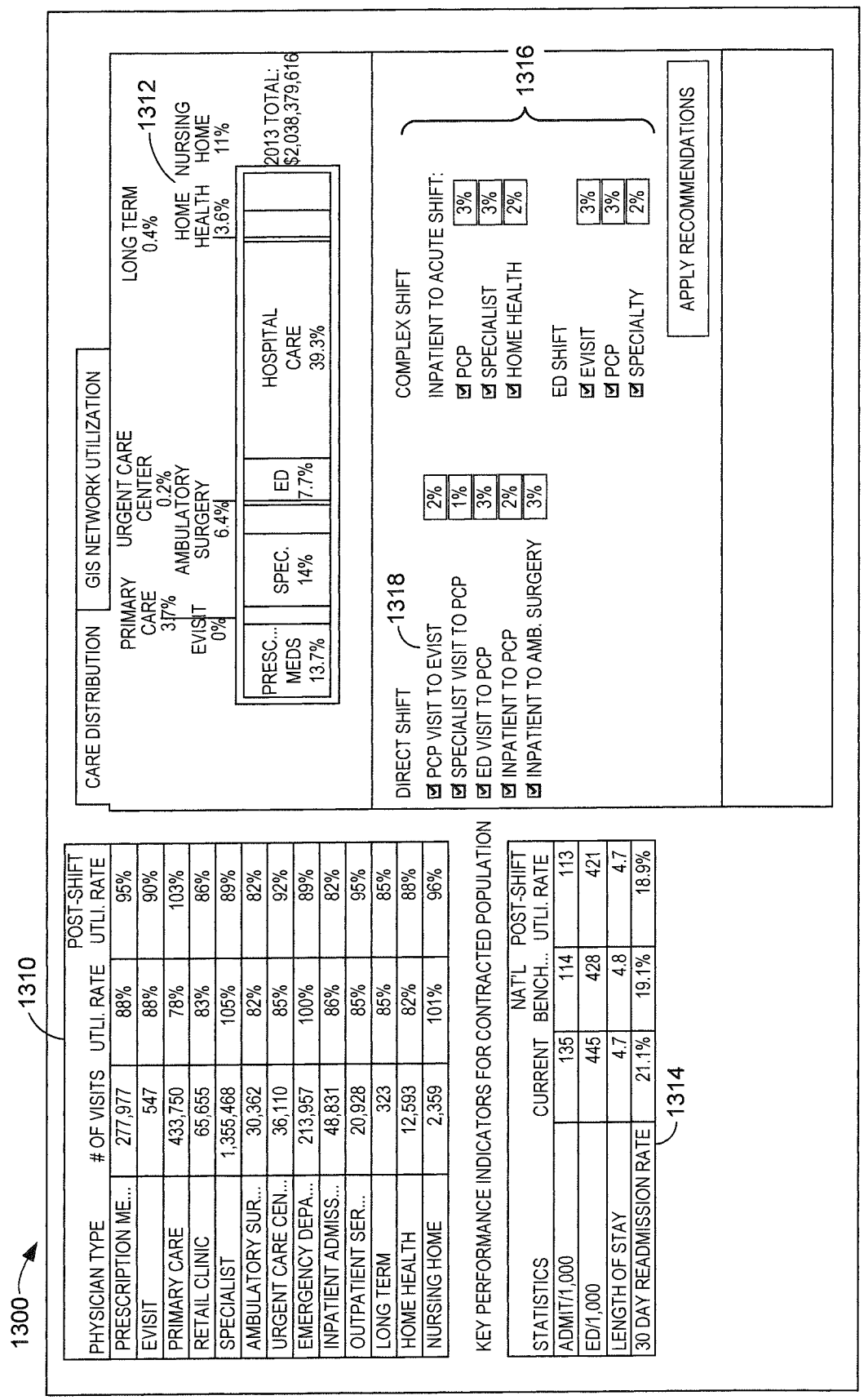
FIG. 13 is an exemplary graphical user interface for presenting current patient utilization by provider type and recommendations for improving current patient utilization by provider type in accordance with an embodiment of the present invention.
Figure 14:
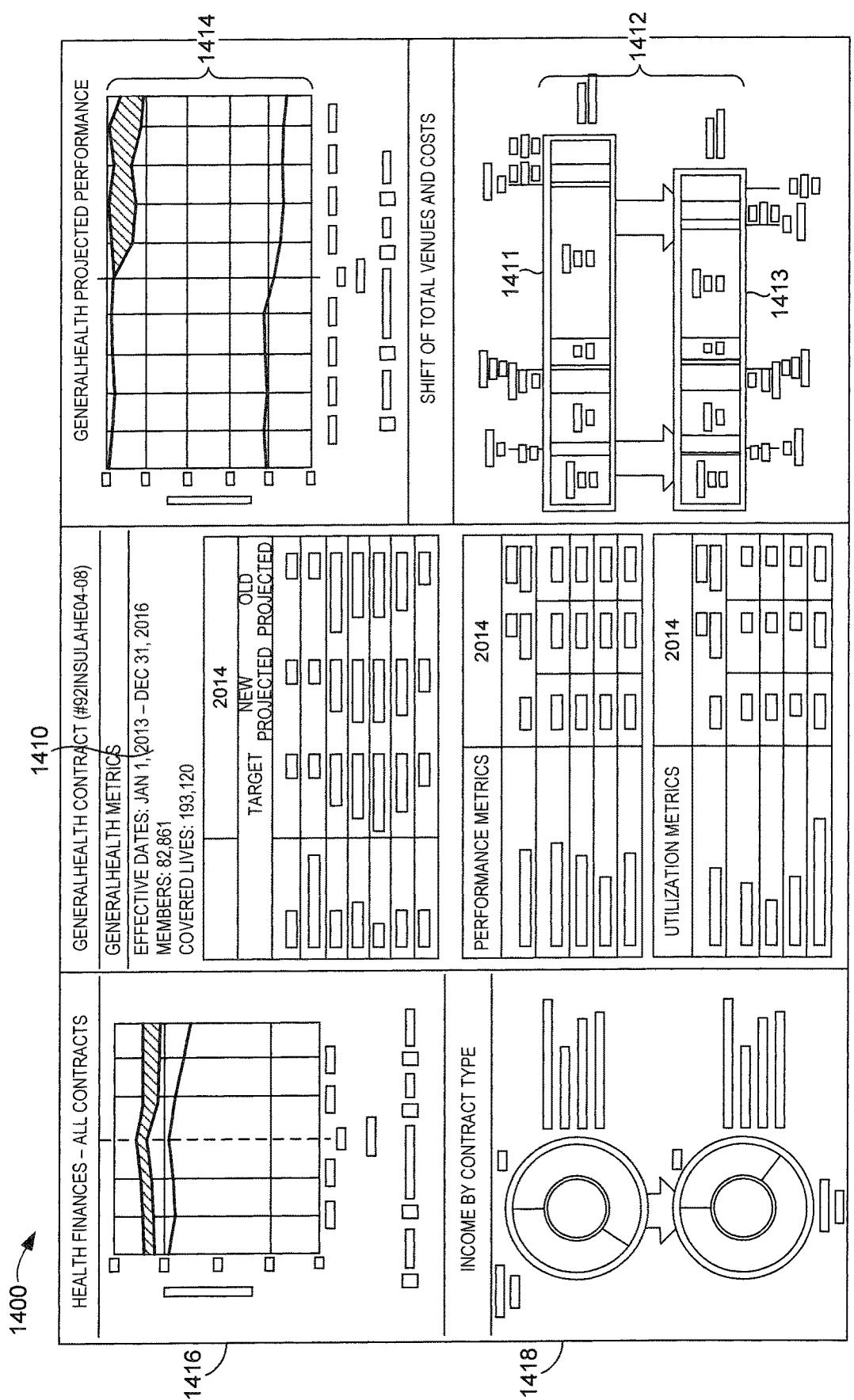
FIG. 14 is an exemplary user interface for presenting projected outcomes for a healthcare organization upon selection of generated venue-shifting recommendations in accordance with an embodiment of the present invention.

The information generated by the contract and organization management program may be presented to the organization on one or more user interfaces (UIs) as shown in FIGS. 12-14. FIG. 12 depicts an exemplary UI 1200 presenting information generated by the contracts and organization management program discussed above. The organization is able to view data related to current contract performance. For example, at area 1210, target and actual performance data is presented for the current year. The target and actual performance data 1210 pertains to a current contract between the organization and a payer and includes financial data 1212, performance metric data 1214, and utilization data 1216. The organization is also able to view data related to future contract performance at area 1218. Future contract performance 1218 may be based, in part, on current or historical contract performance. Future contract performance 1218 includes target and projected financial data 1220, performance metric data 1222, and utilization data 1224. Area 1226 of UI 1200 presents the top ten conditions with the greatest expenditures. This helps the organization to visualize what measures need to be implemented to reduce these costs. Area 1228 provides a breakdown of the organization's current finances.

FIG. 13 depicts a UI 1300 that provides an overview of current care distribution and recommendations generated by the contracts and organization management program. Area 1310 presents a table overview of utilization by provider type; a bar graph 1312 depicts this same information in graphical form. From table 1310, it can be seen, for example, that the organization's specialists, emergency department (ED), and nursing home are being utilized at capacity or are over capacity. Area 1314 presents key performance indicators for patients covered by a particular payer contract and/or for all patients covered under payer contracts. The key performance indicators 1314 are compared to national benchmarks.

Area 1316 presents selectable recommendations automatically generated by the contract and organization management program. The recommendations address areas of concern as indicated by the organizational and patient data. In one aspect, the recommendations comprise venue shifting or provider shifting recommendations where a different care scheme other than the existing care scheme is recommended. The venue shifting or provider shifting recommendations are based on organizational data for the specific healthcare organization. For example, as shown at numeral 1318, the system has made a recommendation that 2% of primary care physician visits be shifted to eVisit (e.g., contacting a patient electronically to determine how the patient is doing) based on current care distribution information. This recommendation leverages organization information indicating that the healthcare organization has capabilities to implement eVisits. The organization can select which recommendations it would like to implement and additional graphical representations showing the impact of the selected recommendations are generated and presented as shown in FIG. 14.

FIG. 14 depicts an exemplary UI 1400 illustrating the effects of selected recommendations on future performance. UI 1400 includes area 1410 that highlights the target projections for the next billing year, original projections, and new projections based on the implementation of selected recommendations broken down by financial data, performance metric data, and utilization data. Area 1412 presents a bar graph 1411 of utilization by provider type for the current year and a bar graph 1413 of projected utilization by provider type for the next billing year based on selection of recommendations. Area 1414 is a graph showing financial savings related to a particular payer contract based on the implementation of recommendations, and area 1416 depicts a graph showing financial savings related to all of the organization's contracts based on the implementation of the recommendations. Additionally, area 1418 depicts a graphical representation of the difference in income by contract type between the current year and the next billing year based on the implementation of the selected recommendations.

Continuing, another program is an outreach program (not shown in FIG. 2) that automatically and without human intervention identifies providers and/or patient population segments eligible for one or more outreach events and executes the outreach event. An outreach event can be defined as an action or communication by the organization or its providers to contact providers or patients regarding one or more quality measures. The outreach events may be tied to, for example, quality measure contract objectives embodied in payer contracts established between a healthcare organization and one or more payers or embodied in contracts or agreements between the organization and its associated providers. For instance, a quality measure contract objective may state that 90% of women over the age of 40 be notified that they should schedule a mammogram. Generating and sending a communication to eligible women would meet this quality measure contract objective.

Figure 15:
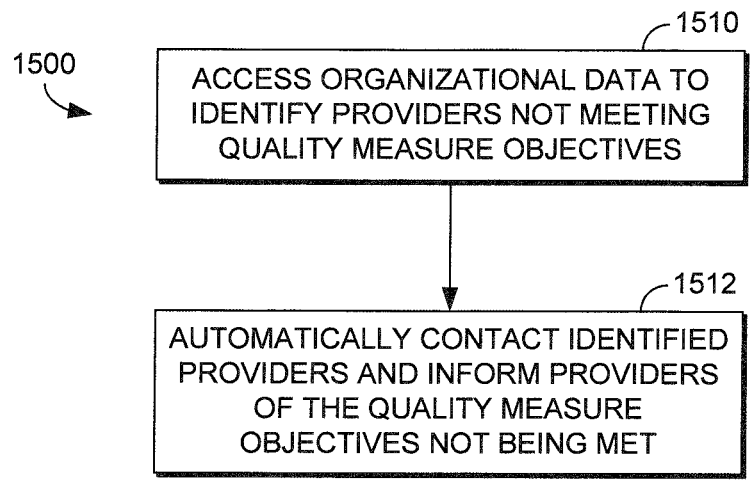
FIG. 15 is a flow diagram of an exemplary method of intra-organization outreach in accordance with an embodiment of the present invention.

Turning to FIG. 15, FIG. 15 depicts a flow diagram of an exemplary method 1500 of performing intra-organization outreach. Intra-organization (e.g., within the organization) outreach enables the organization to automatically identify and contact those providers who are failing to meet one or more quality measure objectives. At a step 1510, organizational data, such as the provider directory 226 of FIG. 2, is accessed to identify providers who are currently not meeting quality measure objectives and the identity of those quality measure objectives. Additional data about the provider may be accessed at this point such as preferred method of communication. At a step 1512, an outreach event is automatically generated for those providers identified as not meeting one or more quality measure objectives. The nature of outreach event may be based on, for example, the provider's preferred method of communication and include a communications such as a printed letter, email, text, call, and the like. The outreach event may include automatically generating the content of the letter, email, text, or call. The content, in turn, informs the provider of what quality measure(s) is not being met, a current percentage of completion, and actions that can be taken by the provider to meet the quality measure(s).

Figure 16:
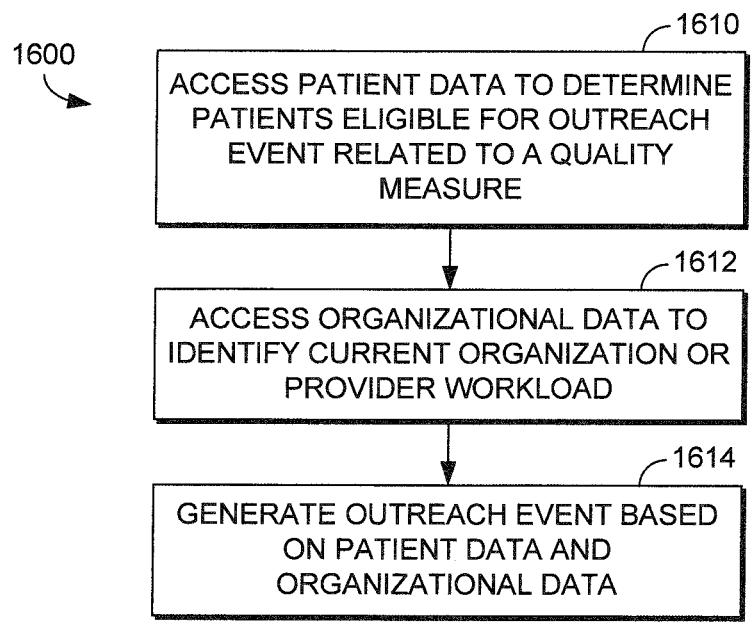
FIG. 16 is a flow diagram of an exemplary method of generating outreach events for an identified patient population segment in accordance with an embodiment of the present invention.

FIG. 16 depicts a flow diagram of a method 1600 of executing outreach events to patients associated with a healthcare organization or a provider. At a step 1610, patient-centric longitudinal population records stored in association with, for example, the population data store 234 of FIG. 2, are accessed to identify patients currently associated with the organization or the provider who are eligible for an outreach event related to one or more quality measures. A patient is eligible for an outreach event if the patient has not yet met one or more quality measures as specified by the organization, contracts, or providers. Once identified, additional patient information is accessed such as preferred mode of communication, patient preferences, social history, family support, and the like.

At a step 1612, organizational data is accessed from, for example, the organization directory 224 and the provider directory 226 of FIG. 2. Organizational data may include current organization workload, current provider workload, operating hours, location information, accessibility information, and the like. At a step 1614, the outreach event is automatically generated based on the patient information and the organizational data. The outreach event may comprise a communication such as a printed letter, a text message, an email, or a phone call, the selection of which is based, in part, on communication preferences associated with the patient. The content associated with the communication includes an identification of the quality measure(s) that has not been met, and information on how to accomplish the quality measure. Information on how to accomplish the quality measure is customized based on the organizational data and the patient data. For instance, if the outreach event relates to a quality measure such as scheduling an appointment for a test, the organizational data is used to determine appointment times that are available and that meet expressed patient preferences.

A record of attempts to contact the patient is maintained. This information is useful to establish an audit trail that may allow the provider and/or the organization to be excused from meeting a certain quality measure contract objective. For example, contract terms may provide that performance of a quality measure contract objective is excused or considered met if the provider or organization makes a certain number of attempts to contact the patient. Keeping a record of attempted patient contact is important for meeting this type of contract term.

For patients who qualify for multiple outreach events related to different quality measures, the method 1600 is adapted to synthesize the multiple different quality measures and generate a single outreach event or communication related to the multiple different quality measures using the organizational data and the patient data. For example, a person may need to have his or her blood drawn for hemoglobin A1C testing as well as receive a mammogram. Organizational data and patient data is used to generate a single communication that addresses both of these quality measures and includes, for example, a single time frame and/or location that enables the patient to accomplish both of these quality measures and that further meets the patient's preferences.

Returning to FIG. 2, another program is an intervention program 246 that generates stateful workflows to reduce condition-specific risk or to improve outcomes of patients in the identified segment that have the condition. As with the output of the other programs, the output of the intervention program 246 is specific to the healthcare organization. By way of illustrative example, a first healthcare organization may have contractual provisions with a payer that stipulates that the organization will be reimbursed for the use of health coaches to monitor medication compliance. A second healthcare organization may have contractual provisions with a payer that stipulates that the organization will not be reimbursed for the use of health coaches in monitoring medication compliance. When generating a workflow to monitor medication compliance amongst diabetic patients, a workflow for the first organization would utilize the health coaches to call the patient on a daily basis to make sure the patient is taking the correct medication. On the other hand, a workflow for the second organization would generate, for example, an email that is sent to the patient reminding the patient to take his/her medication. These workflows are stored in an action data store 256 that is available for use by the healthcare organization.

An additional program may include a measurement program 242 that measures various outcomes associated with the identified population segment. Outcomes may include, for example, readmission rates, medication compliance rates, re-infection rates, patient satisfaction results, compliance with standards-of-care, and the like. The output of the measurement program 242 is stored in association with a measures data store 252 that is available for use by the healthcare organization to improve quality control measures, etc. The information may also be utilized by payers to determine rates of reimbursement. For instance, a payer may have incentive reimbursements if readmission rates are kept below a predefined threshold. In another example, reimbursement rates may be reduced if the patient satisfaction results are poor. Any and all such aspects are contemplated as being within the scope of the invention.

As mentioned the output of the programs 238, 240, 242, 244, and 246 and the other programs set forth above may be used by a healthcare organization via one or more computer applications in a variety of ways. Some examples include using the data to initiate alerts, provide access to patient records, create patient lists or registries, generate summary pages, initiate quality control measures, and the like. Another example is a score card application that utilizes a builder program to enable the organization to build a scoring plan for itself, its providers, its payers, and/or its patients and present the results of the score plan on one or more score card user interfaces. Execution of the score card application leverages the organizational data, the patient-centric longitudinal population records, and the output of some or all of the programs outlined above.

Figure 17:
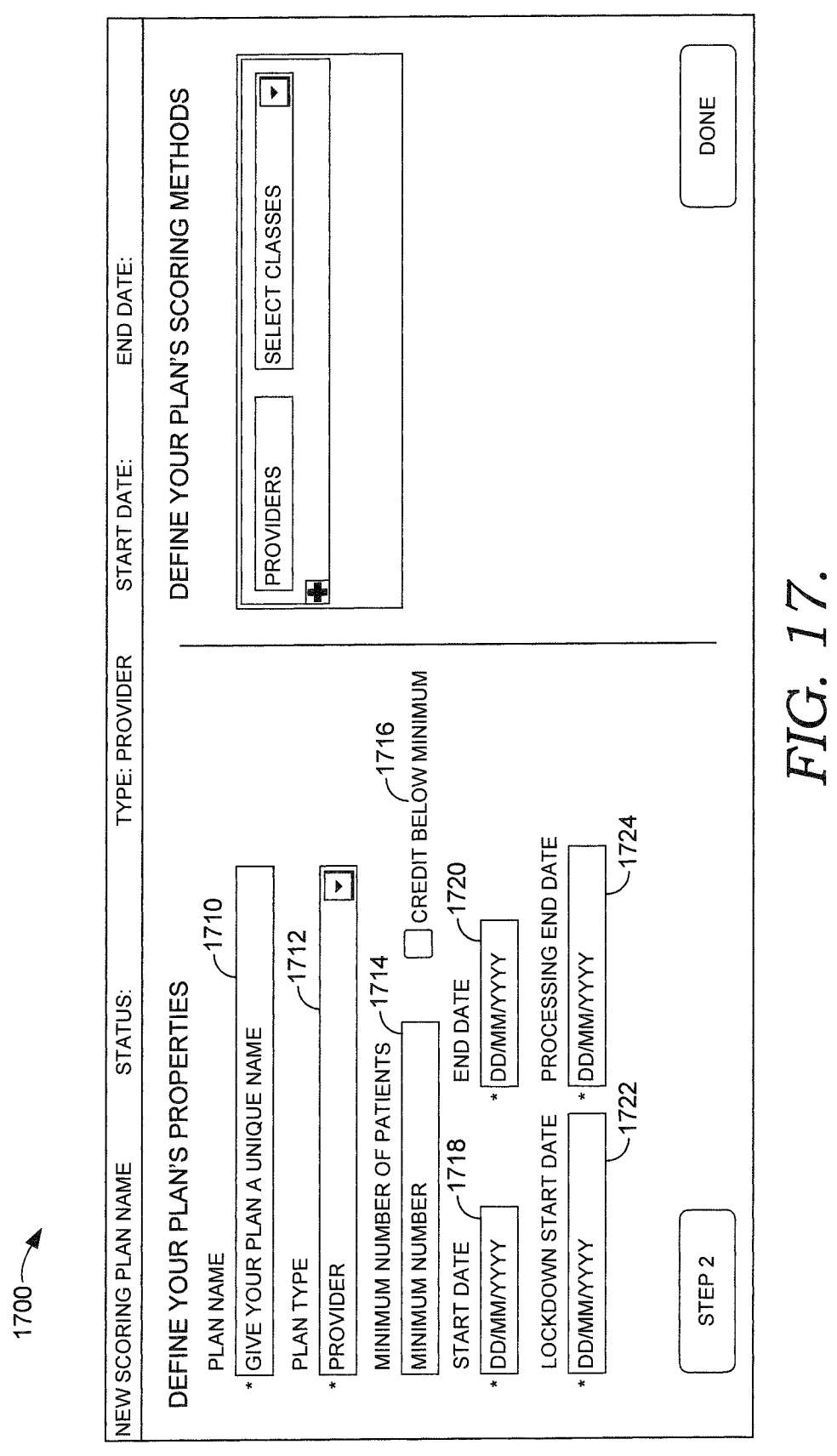

With respect to the builder program for the score card application, FIGS. 17-23 depict exemplary UIs used by a healthcare organization to build score plans for itself, its providers, its payers, and/or its patients. FIG. 17 depicts a start-up page 1700 for defining the score plan properties. Input fields are provided that enable a healthcare organization to enter textual data or to select from one or more options associated with a particular input field. Input field 1710 is adapted to receive a plan name. Input field 1712 provides options for selecting an entity to score or enroll in the score plan. Options include an organization, provider group, provider, payer, and/or patient. Input field 1714 enables the organization to specify a minimum number of patients that should be part of a scoring group for a quality measure in order for that quality measure to count towards the entity's overall score. Selection of input field 1716 credits the entity for the quality measure even though there is not the minimum number of patients in the scoring group. Input fields 1718 and 1720 enable the organization to specify a scoring period for the entity by indicating start and end dates for the scoring period. Because data, such as claims data, may still be received and processed after the designated end date, input fields 1722 and 1724 enable the organization to specify a lockdown start date and a processing end date.

Turning to FIG. 18, FIG. 18 depicts an exemplary UI 1800 that enables the organization to set up categories and associate quality measures with those categories. A category can be entered into input field 1810. Categories represent logical groupings of quality measures. The category 1810 may be selected from a set of predefined categories or organization-specific categories. A list of organization-specific or standardized quality measures is presented in area 1812. The quality measures 1812 may be customized based on the category 1810. Each of the quality measures 1812 includes an "Add" option by which it can be associated with the category 1810. For instance, the organization could select quality measures 1814 and 1816 and associate them with the category 1810.

FIG. 19 depicts an exemplary UI 1900 presented after a selection of the quality measures 1814 and 1816 on UI 1800. UI 1900 includes the category 1810 as well as the added measures 1814 and 1816. The quality measures 1812 continue to be presented so that the organization is able to associate additional quality measures with the category 1810.

Figure 20:
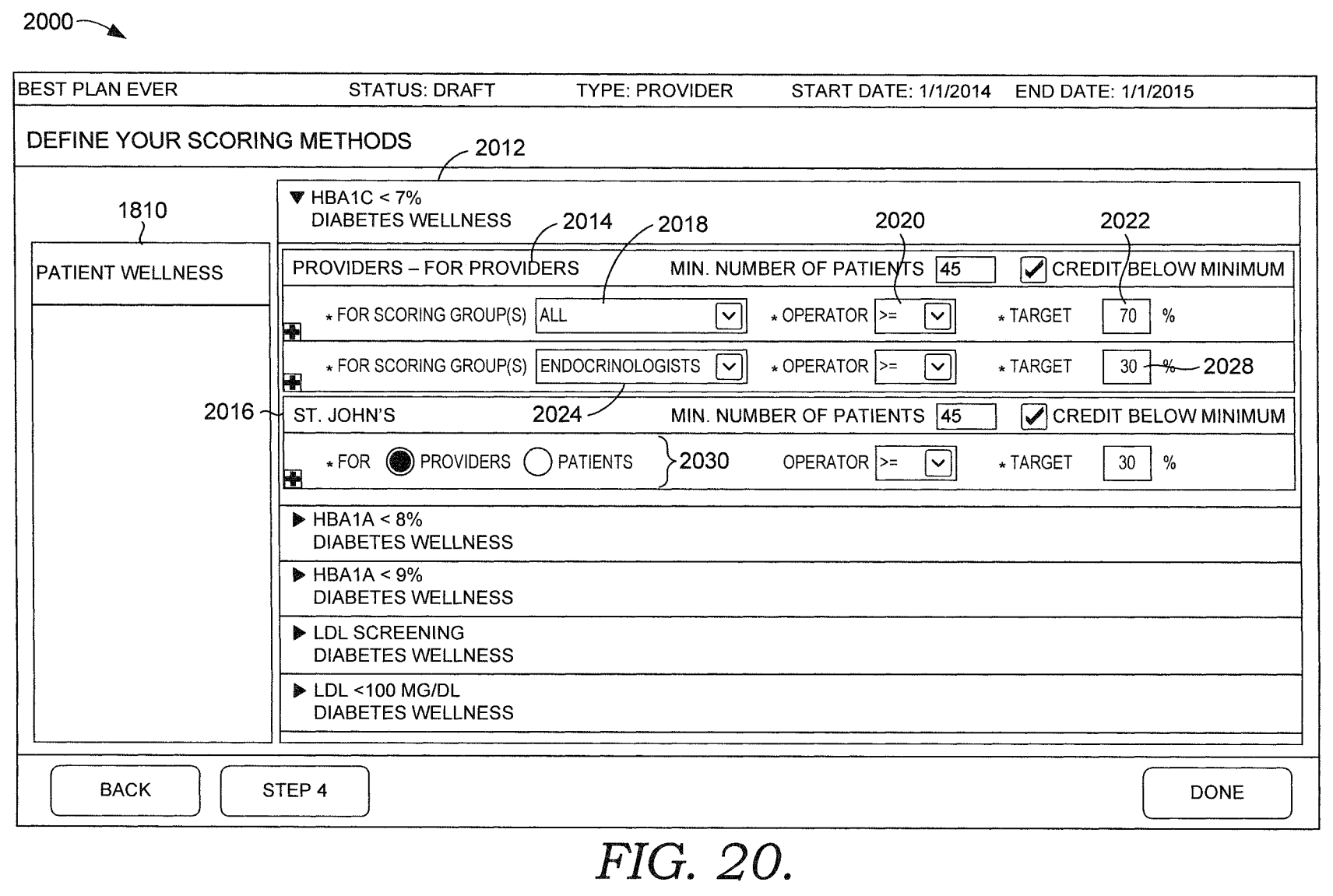

FIG. 20 depicts an exemplary UI 2000 that enables the organization to designate targets for each of the selected quality measures. FIG. 20 includes the category 1810. Additionally, the UI 2000 includes a quality measure 2012 (e.g., HbA1C<7% which is a measure of wellness in diabetics). The area under the quality measure 2012 has been expanded so that the organization can select providers, payers, organizations, and/or patients to score. For instance, the organization can select providers or provider groups to score in area 2014, and an organization to score in area 2016 for the quality measure 2012. With respect to the providers 2014, the organization has elected to set targets for the quality measure 2012 for all providers at field 2018 (by selecting from a list of options) and also specifically for endocrinologists at input field 2014 (by selecting from a list of options). For all the providers 2018, the organization selects a mathematical operator at input field 2020. Mathematical operators includes such things as greater than, less than, equal to, greater than or equal to, less than or equal to, and the like. At input field 2022, the organization selects a target percentage. Thus, for all the providers 2018, the organization has specified that the providers 2018 meet the quality measure of keeping HbA1C levels less than 7% if 70% of the scorable patient group meets this quality measure. For the endocrinologists 2024, the organization has elected to lower the target 2028 to 30% because this specialty may treat more uncontrolled cases of diabetes and it would be unlikely for this group to have 70% of the patients in the scorable patient group meet the quality measure.

With respect to the organization 2016, options are provided for scoring the organization by providers or patients at area 2030. Like with providers 2014, operators and targets can be selected or inputted. Thus, as shown in FIG. 20, if "providers" is selected at area 2030, the organization 2016 would meet the quality measure if 30% of the providers met the goal of keeping HbA1C levels less than 7% for their diabetic patients. If "patients" is selected at area 2030, then the organization 2016 would meet the quality measure if, for example, 30% of the scorable patient group at the organization have HbA1C levels less than 7%.

FIG. 21 depicts an exemplary UI 2100 presented after information has been inputted/selected on UI 2000. The UI 2100 includes many of the same elements as the UI 2000 but additionally includes, for example, "points" input boxes 2122 and 2126, and "calculated percent of total score" 2124 and 2128. The points input boxes 2122 and 2126 enable an organization to assign a number of points to, in this case, providers 2018 and endocrinologists 2024 if the designated quality measure is met. The amount of points accumulated by a provider at the end of a scoring period generally affects incentive amounts and/or reimbursement amounts. After the points are entered in, for example, the input box 2122 for the providers 2018, a calculated percent of total score is presented at 2124. This feature enables the organization to understand the impact of an assigned score on the provider's total score and to adjust accordingly. For instance, the endocrinologists 2024 will likely be scored on fewer items than the providers 2018. Thus, assigning, for example, 2 points to the endocrinologists 2024 at box 2126 may significantly impact the percent of total score 2128 for the endocrinologists 2024 (i.e., it may be 20% of the endocrinologists' score compared to 2% of the providers' score). UI 2100 also includes a "weight" box 2130 associated with the category 1810. The weight box 2130 enables the organization to weight categories.

FIG. 22 depicts an exemplary UI 2200 after points have been entered and the percent of total score has been calculated. As shown, 2 points have been entered in box 2122 for the providers 2018, which is 2% of their total score as shown at 2124. By contrast, the two points entered in box 2226 for the endocrinologists 2024 is 20% of their total score as shown at 2128. The organization may reconsider how many points to score the quality measure 2012 for the endocrinologists 2024 based on this.

FIG. 23 depicts an exemplary UI 2300 presenting a summary page of the information inputted on the previous builder screens. The UI 2300 includes a sorting area 2302 by which the organization can sort by organization, provider group, provider, and/or patient for each quality measure. The outcome of the sorting is shown at 2312. The score plan builder may also include a UI that presents all of the score plans currently being drafted and/or used by the healthcare organization. A user could select one of the plans to view the plan and/or edit the plan.

Figure 24:
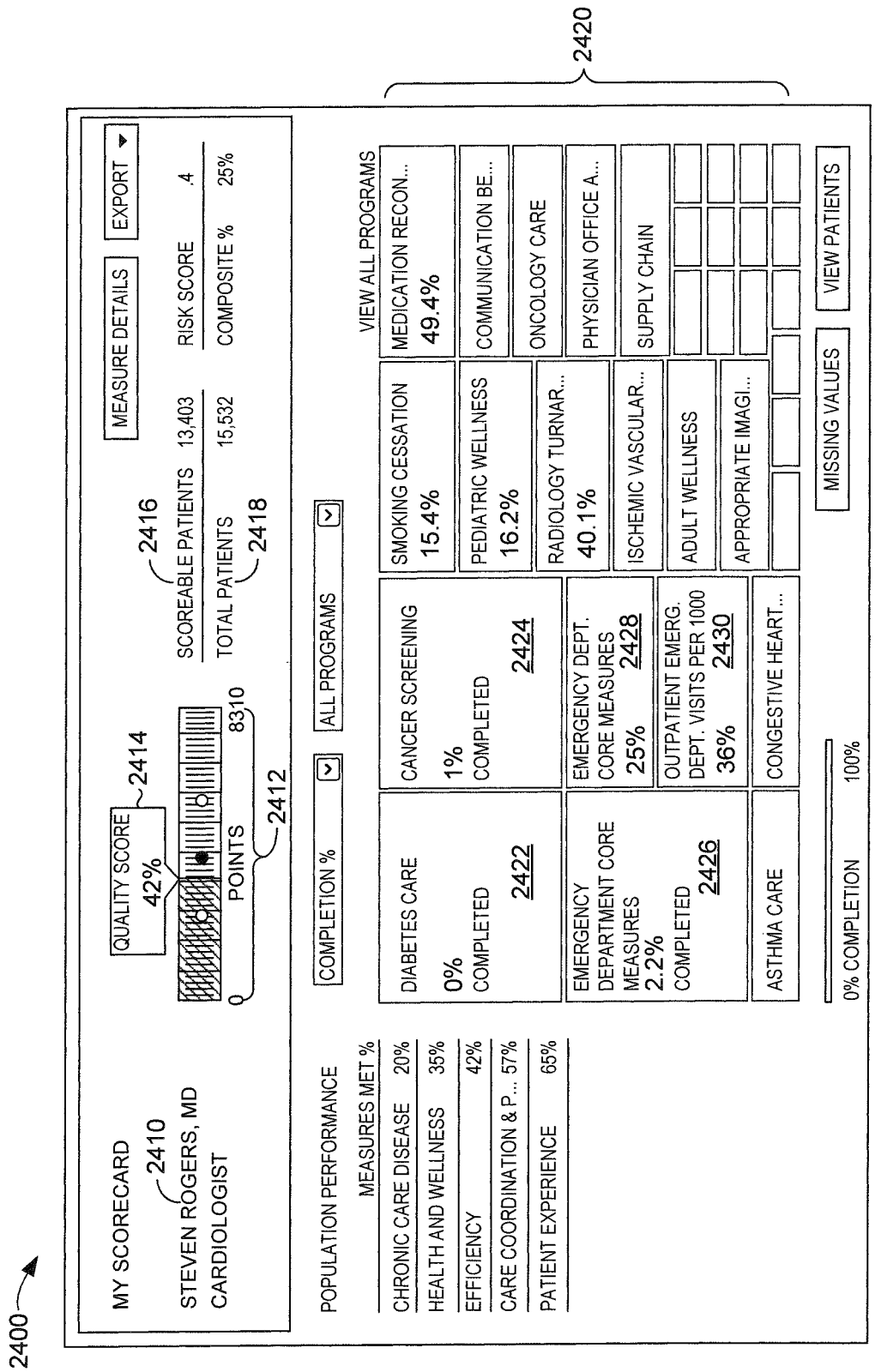
FIGS. 24-25 depict exemplary provider score plan user interfaces for enabling providers to track progress towards reaching a scoring goal in accordance with embodiments of the present invention.

Once the score plan has been built and implemented, the results are presented on score card UIs. The score card UIs may be configured to present outcome data that is relevant to a provider, a provider group, and/or the organization as a whole. One example of a provider score card is depicted in FIG. 24. FIG. 24 illustrates an exemplary provider score card UI 2400 that presents information related to a particular provider's progress towards achieving a maximum number of total points as determined by the score plan builder for that particular provider. As mentioned, the total score and/or percentage completion towards the total score may be used to determine reimbursements and/or incentives for the provider. The UI 2400 includes the provider name 2410 and a bar graph 2412 graphically illustrating the provider's progress towards reaching his maximum number of points. As seen at 2414, the provider 2410 is 42% of the way to achieving his maximum number of points. A total number of patients attributed to the provider 2410 is shown at 2418, and the number of patients in scorable patient groups attributed to the provider is shown at 2416. Area 2420 depicts a treemap of all of the quality measures against which the provider 2410 is being scored. A treemap displays hierarchical information in a series of clustered rectangles, which together represent a whole. The size of each box represents a quantity (either proportionately or inversely). The rectangles may be colored differently and have different color intensities to indicate the relative degree of importance of a particular rectangle in comparison to the other rectangles in the treemap. Information may be directly displayed in the rectangles, the information may be revealed upon interaction with the rectangles, or a combination of both.

The UI 2400 depicts the top five quality measures 2422, 2424, 2426, 2428, and 2430 for which the provider 2410 is demonstrating the least progress towards completion, thus enabling the provider 2420 to quickly assess areas for improvement. The quality measures 2422, 2424, 2426, 2428, and 2430 are presented in the largest rectangles to help draw the user's attention. For instance, with respect to the quality measure 2422 "Diabetes Care," the provider 2410 is 0% of the way towards achieving the total score for this quality measure 2422. Additional information may be presented upon hovering over the various rectangles. For instance, the number of patients in the scorable patient group for the particular quality measure may be presented, along with the number of patients in the scorable patient group who have achieved the particular quality measure. The determination of which top five quality measures to present on the UI 2400 is determined by the system. The system may base its determination of the top five quality measures 2422, 2424, 2426, 2428, and 2430 based on not only the percent progress towards completion, but also the number of patients in the scorable group, the impact of achievement of the quality measure on the provider's overall total score with the least amount of effort, and the like.

Figure 25:
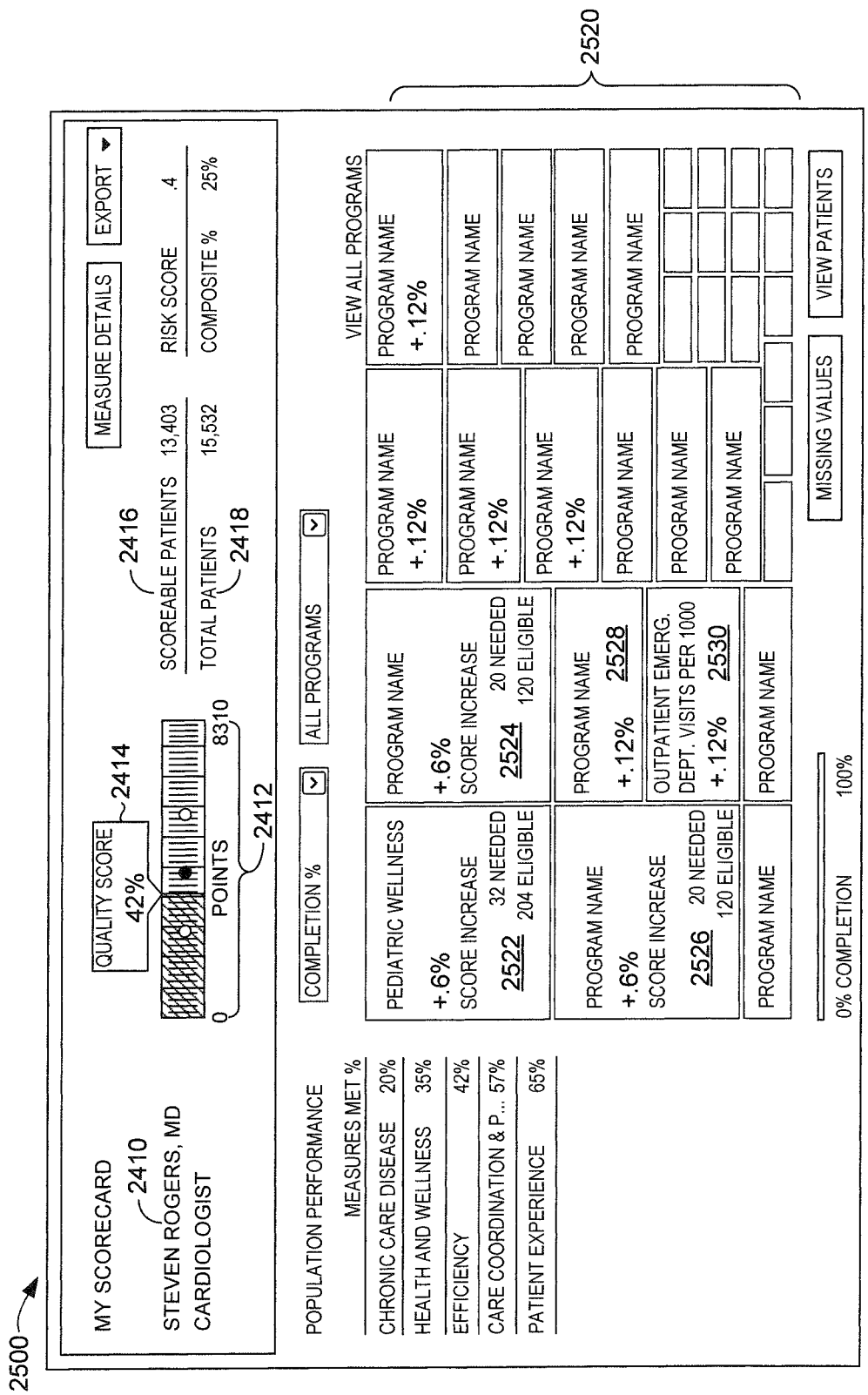

FIG. 25 depicts another exemplary provider score card UI 2500 that presents scoring information in the form of opportunity indexes. The concept of an opportunity index is useful when a provider is at the beginning of his/her scoring period. At the beginning of the scoring period, a provider will naturally not have achieved any completion towards meeting his or her scoring goal. Thus, it is not particularly useful to present the top five quality measures that need improvement. Instead, the system determines quality measures that may be difficult for the provider to achieve—these are known as opportunity index quality measures. One example of a quality measure that may be difficult for a provider to achieve is threshold-based measures where a particular quality measure is required to be maintained within a certain range. For instance, the quality measure of keeping hemoglobin A1C levels less than 7% for diabetic patients not only requires that the diabetic patient come in for blood draws, but also requires medication and diet supervision on the part of the provider and the patient. Other types of quality measures that may fall within the opportunity index type include quality measures that were missed by the provider in the previous scoring period and/or new measures that the provider has never been scored against. Compare these types of quality measures to a quality measure requiring a provider to contact a patient to schedule a mammogram. This type of quality measure requires little effort on the part of the provider and may be easily obtainable.

The UI 2500 contains some of the same elements as the UI 2400 and like numbering is used to label these elements. The UI 2500 includes a treemap 2520 displaying all of the quality measures against which the provider 2410 is being scored. Instead of percentage of completion information being presented however, opportunity index information is presented in association with the quality measures. The information in the UI 2500 is useful at the beginning of the provider's scoring period and enables the provider 2410 to quickly see what areas offer the most opportunity to improve the provider's overall score. The top five opportunity index quality measures as determined by the system are shown in as 2522, 2524, 2526, 2528, and 2530. The quality measures 2522, 2524, 2526, 2528, and 2530 are presented in the largest rectangles to draw the user's attention. Using the quality measure "Pediatric Wellness" 2522 as an example, the provider 2410 has an opportunity to improve his overall score by 0.6% if he meets this quality measure. The provider scorecard UI 2500 may dynamically shift to the provider scorecard UI 2400 as the scoring year progresses allowing the provider to see where he or she can improve with the least amount of effort.

Figure 26:
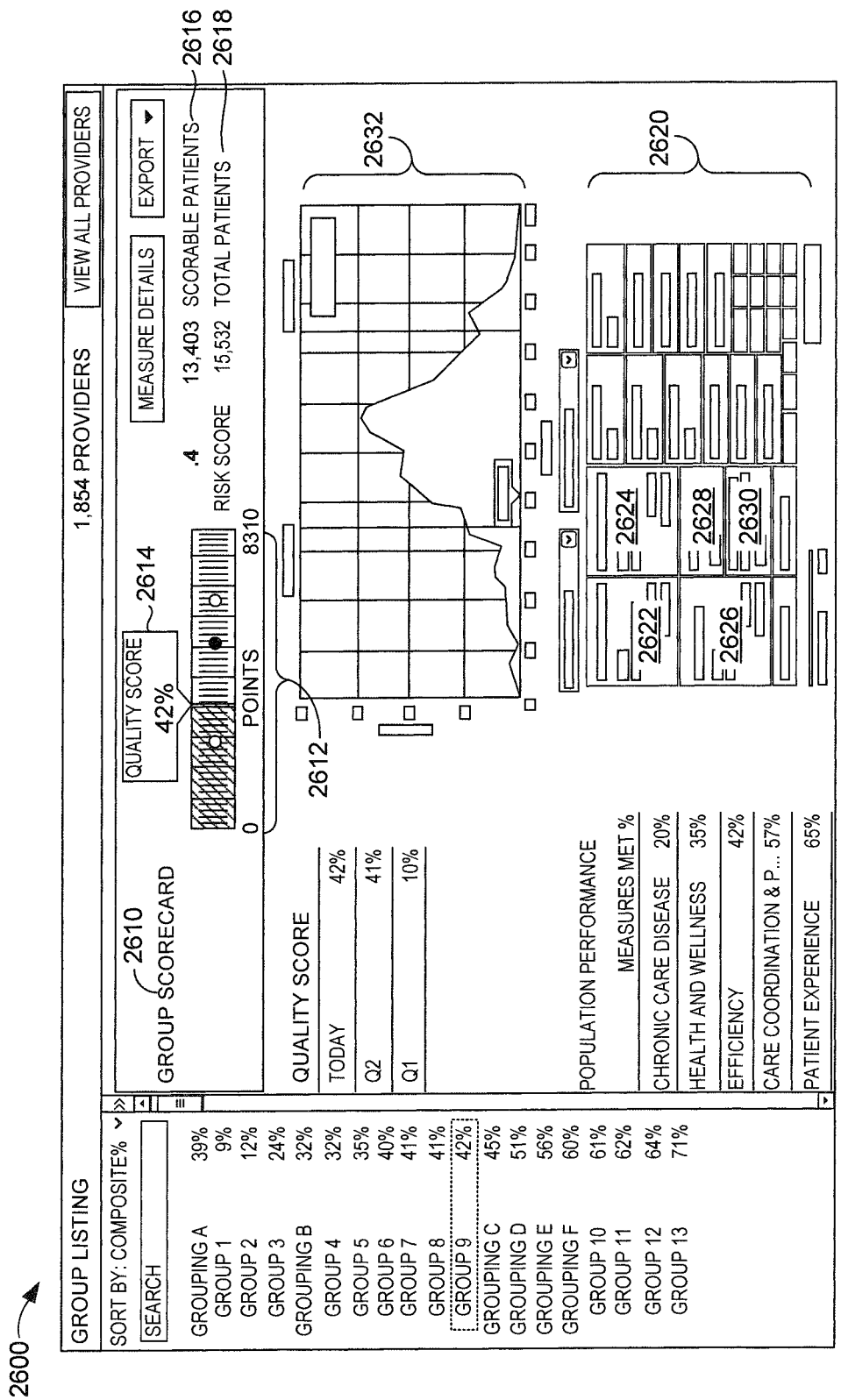
FIG. 26 depicts an exemplary score plan user interface used by a healthcare organization to track a provider group's progress toward reaching a scoring goal in accordance with embodiments of the present invention.

Score cards can also be generated at a provider group level and/or organization level. FIG. 26 depicts an exemplary provider group scorecard UI 2600 that may be used by an organization to see how a particular provider group is performing with respect to one or more quality measures against which the group is being scored. This may be useful to the organization, for example, when determining whether to renew the provider group contract.

The UI 2600 includes the provider group name 2610 as well as a bar graph 2612 that illustrates the percentage towards completion of the total number of scorable points for the provider group 2610. For example, the provider group 2610 is 42% towards completion of the total number of scorable points (indicated by element 2614). The UI 2600 also indicates the total number of patients 2618 attributed to the group 2610 and the total number of patients in scorable patient groups 2616 attributed to the group 2610.

A treemap 2620 is presented that includes all of the quality measures against which the provider group 2610 is being scored. Like the UI 2500, the top five opportunity index quality measures 2622, 2624, 2626, 2628, and 2630 are presented along with opportunity index percentages. The treemap 2620 may be presented at the beginning of the provider group's scorable year and dynamically transition to a treemap similar to the UI 2400 that displays percentage toward completion data as the scoring year progresses. The UI 2600 also includes a graph 2632 displaying trending information regarding the completion of quality measures by the provider group.

Although not shown, it is contemplated that score cards could be generated that display quality measure information about individual patients. This may be useful when a patient attributed to a provider suffers from multiple medical conditions that place him or her into multiple quality measure scorable patient groups. Patients of this type may have a large impact on the provider's total score, and the provider would be interested in knowing what quality measures associated with the patient may be most difficult to meet (e.g., at the beginning of the provider's scoring year), and/or which of the patient's quality measures could be improved with the least amount of effort by the provider (e.g., later in the provider's scorable year). Information on the patient's quality measures could be presented in the form of a treemap as shown in UIs 2400, 2500, and 2600.

Figure 6:
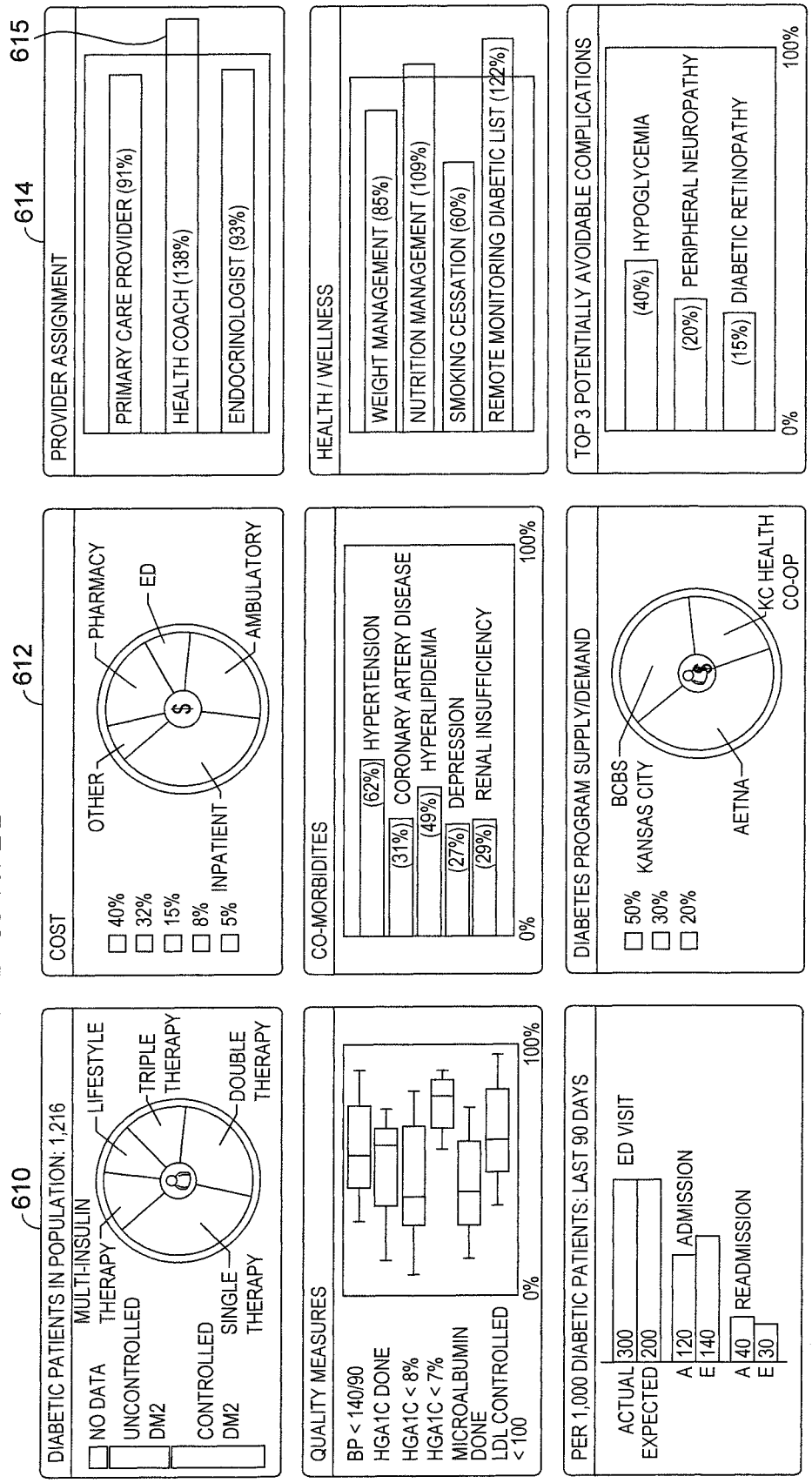
FIG. 6 is an exemplary graphical user interface suitable to generate a predictive model of population health data for a healthcare organization in accordance with an embodiment of the present invention.

In one aspect, a healthcare organization can run the programs outlined above in a demonstration mode and generate a projected set of data for analysis. FIG. 6 is an exemplary graphical user interface demonstrating in a graphical form the output of the various programs 238, 240, 242, 244, and 246 with respect to a population segment that has diabetes mellitus type 2. Area 610 provides a breakdown of the identified population segment, and area 612 provides a breakdown in costs associated with care according to different facilities and/or divisions within the healthcare organization. Area 614 graphically presents a breakdown in provider assignment or attribution. As can be seen, the program projected that health coaches 615 will consume 138% of provider assignments. Based on this information, the healthcare organization can modify the program template (using, for example, the template building area 512 of FIG. 5). Thus, instead of actually implementing the population health management program and noting its problems, a healthcare organization can view the projected problems beforehand and implement the needed modifications to the templates.

The population health management system 200 is an closed-loop system meaning that as a healthcare organization utilizes the output of the programs outlined above, more organizational and patient data is generated which is fed back into the system 200 and used to update the various data stores. Further, the system 200 operates over and is compatible with existing electronic medical record systems associated with healthcare organizations, even if these electronic medical record systems are disparate in nature. Thus, a healthcare organization can utilize the system to manage population health without having to incur significant financial costs to reconfigure its already-existing electronic medical record system.

Turning now to FIG. 3, an exemplary flow diagram is depicted of a method 300 of enabling a healthcare organization to manage population health. At a step 310, a condition-specific program template is extracted from, for example, a network management service such as the network management service 210 of FIG. 2. The extraction of the condition-specific program template may be accomplished by a compiler such as the compiler 236 of FIG. 2. The condition-specific program template may have been automatically generated by the network management service, manually created by, for example, a programmer associated with a healthcare organization, or automatically created and modified by a user. In one aspect, the condition-specific program template is constructed using a population-health specific programming language. The program templates are configured to identify population segments that have a particular condition or are at risk for developing the condition, and stratify patients within the population segment based on, for example, degree of severity or risk, financial factors, demographic factors, and the like. The condition-specific program templates are also configured to attribute patients within the segment to healthcare providers, generate workflows designed to improve outcomes and/or reduce risk, and measure intervention outcomes.

Once the condition-specific program template is extracted at the step 310, it is customized or localized to a particular healthcare organization at a step 312. Customization includes taking into account the organizational data associated with the healthcare organization. This data may be stored in data stores such as the contracts data store 222, the organization directory data store 224, and the provider directory data store 226 of FIG. 2. The organizational data may include healthcare facilities associated with the healthcare organization, healthcare providers associated with the healthcare organization, and contractual provisions between the healthcare organization and its associated payers. At a more granular level, organizational data includes provider names, credentials, geographic location of providers and healthcare facilities, operating hours, capabilities, clinical and financial objectives associated with the contracts, and the like. At a step 314, the customized program template is communicated to a program engine such as the program engine 214 of FIG. 2.

FIG. 4 depicts a flow diagram of an exemplary method 400 of managing population health and may be seen as a continuation of the method 300. At a step 410, the program engine receives the customized condition-specific program templates from the compiler. And, at a step 412, the program engine receives patient data from, for example, a population management service such as the population management service 212 of FIG. 2. Patient data includes diagnoses, demographic information, insurance or payer information, location information, preference information, and clinical data such as lab results, X-rays, procedure results, clinical notes, and the like.

At a step 414, the program engine executes the customized condition-specific program templates against the patient data. The output of the program engine comprises population health data that can be used by the healthcare organization to manage the health of a population segment. For instance, the program engine may generate a list of patients associated with the healthcare organization who are suffering from a disease condition. The patients may be stratified by disease severity, and the patients may be attributed to one or more providers associated with the healthcare organization who can efficiently manage the disease condition. Workflows may be generated to improve outcome and efficiently utilize the attributed healthcare providers. Intervention outcomes are measured; these outcomes may be used by payers to determine an amount of reimbursement to the healthcare organization.

The present invention has been described in relation to particular embodiments, which are intended in all respects to be illustrative rather than restrictive. Further, the present invention is not limited to these embodiments, but variations and modifications may be made without departing from the scope of the present invention.

What is claimed is:

1. One or more non-transitory computer-readable media having computer-executable instructions embodied thereon that, when executed by a processor of a computing device, cause the processor to perform actions comprising:
    transforming raw data associated with a plurality of patients from a plurality of data sources, wherein the raw data is in different formats and is transformed into a standard format;
    generating and storing, in a data storage device, population records associated with the plurality of patients based on the transformed data in the standard format, wherein the population records include at least data associated with patient health encounters with an entity;
    running, via a processor, a score card application;
    determining, by the score card application, a score for the entity for a quality measure used for evaluating performance of the entity based on the population records by at least applying the quality measure to the data from the population records, wherein the score is determined using a user defined target score for the quality measure and by assigning a quantity of points to the entity for the quality measure within a particular time period as applied to the data from the population records;

obtaining, from a program engine associated with running the score card application, the score for the entity, the quality measure used for evaluating performance of the entity, and the user-defined target score for the quality measure; and in response to obtaining the score, generating and causing display of a graphical user interface that displays the score for the entity and a graphical representation of the score as a percentage of completion for the quality measure relative to the user defined target score; and displaying an opportunity index value indicating a specific percentage increase to the score that will result from the entity performing a task related to one or more of the plurality of patients, wherein the specific percentage increase to entity score is determined by the score card application associated with the program engine.

2. The media of claim 1, wherein the graphical user interface that is generated displays the percentage of completion as a bar graph, the bar graph representing the score of the entity as the percentage of completion relative to a total value representing 100% completion for the quality measure.

3. The media of claim 1, wherein the graphical user interface that is generated displays the percentage of completion as a bar graph, the bar graph representing the score of the entity as the percentage of completion relative to the user-defined target score for the quality measure, and wherein the user-defined target score is less than a total value representing 100% completion for the quality measure.

4. The media of claim 1, wherein the graphical user interface that is generated displays a total number of patients attributed to the entity and a portion of the total number of patients attributed to the entity, wherein the portion of the total number of patients was used by the score card application to generate the score for the entity.

5. The media of claim 1, wherein the graphical user interface comprises a plurality of display areas for the score card application that uses the program engine to build and execute a scoring program based on user input, the plurality of display areas being configured to display the score for the entity as the percentage of completion for the quality measure relative to the user-defined target score.

6. One or more non-transitory computer-readable media having computer-executable instructions embodied thereon that, when executed, provide a method for generating a graphical user interface, the media comprising:

transforming raw data associated with a plurality of patients from a plurality of medical data sources, wherein the raw data is in different formats and is transformed into a standard format;

generating and storing, in a data storage device, population records associated with the plurality of patients based on the transformed data in the standard format, wherein the population records include at least data associated with patient health encounters with an entity;

determining, as output from a program engine that executes a scoring program via a score card application, an entity score for a plurality of quality measure categories used for evaluating performance of the entity based on the population records by at least applying the plurality of quality measures to the data from the population records, wherein the entity score is determined using a user-defined target score for the plurality of quality measure categories and by assigning a quantity of points to the entity for the plurality of quality measure categories within a particular time period as applied to the data from the population records;

obtaining, as output from the program engine that executes the scoring program via the score card application, the entity score for the entity, an opportunity index value for the entity, the plurality of quality measure categories, and the user-defined target score;

generating and causing display of a graphical user interface that displays:

the entity score;

a graphical representation of the entity score as a percentage of completion for each of the plurality of quality measure categories used in the scoring program to evaluate performance of the entity with respect to the plurality of quality measure categories; and for at least one quality measure category of the plurality of quality measure categories, another graphical representation of the opportunity index value for the entity that is specific to the at least one quality measure category, the opportunity index value indicating a specific percentage increase to the entity score that will result from the entity performing one or more tasks that correspond to the at least one quality measure category, wherein the specific percentage increase to the entity score is determined by the scoring program executed by the program engine.

7. The media of claim 6, wherein the graphical user interface that is generated displays the entity score as a bar graph, the bar graph representing the entity score as the percentage of completion for the plurality of quality measure categories relative to a total value representing 100% completion for the plurality of quality measure categories.

8. The media of claim 6, wherein the graphical user interface that is generated displays the entity score as a bar graph, the bar graph representing the entity score as the percentage of completion for the plurality of quality measure categories relative to the user-defined target score, and wherein the user-defined target score is less than a total value representing 100% completion for the plurality of quality measure categories.

9. The media of claim 6, wherein the graphical user interface that is generated displays a total number of patients attributed to the entity and a portion of the total number of patients attributed to the entity, wherein the portion of the total number of patients was used to generate the entity score.

10. The media of claim 6, wherein for the at least one quality measure category, the graphical user interface that is generated displays a number of patients needed to increase the entity score by the opportunity index value that is specific to the at least one quality measure category.

11. The media of claim 6, wherein the graphical user interface that is generated displays a number of patients needed to increase the entity score to meet the user-defined target score.

12. The media of claim 6, wherein the graphical user interface that is generated displays at least three quality measure categories of the plurality of quality measure categories, and wherein the graphical user interface displays the percentage of completion for each of the at least three quality measure categories.

13. The media of claim 6, wherein the graphical user interface that is generated displays the percentage of completion as individual percentages of completion for each of the plurality of quality measure categories.

14. The media of claim 13, wherein the graphical user interface that is generated displays the individual percentages of completion for each of the plurality of quality measure categories as a treemap having a defined number of clustered rectangles, each of the defined number of clustered rectangles representing one of the plurality of quality measure categories, wherein a size of each of the defined number of clustered rectangles is inversely proportional to the individual percentages of completion for each of the plurality of quality measure categories.

15. The media of claim 13, wherein the graphical user interface that is generated displays the individual percentages of completion for each of the plurality of quality measure categories as a treemap having a defined number of clustered rectangles, each of the defined number of clustered rectangles representing one of the plurality of quality measure categories, wherein a size of each of the defined number of clustered rectangles is proportional to the individual percentages of completion for each of the plurality of quality measure categories.

16. A system comprising:
one or more processors communicatively coupled to a program engine that
executes a scoring program via a score card application, wherein the one or more processors:
transforming raw data associated with a plurality of patients from a plurality of medical data sources, wherein the raw data is in different formats and is transformed into a standard format;
generating and storing, in a data storage device, population records associated with the plurality of patients based on the transformed data in the standard format, wherein the population records include at least data associated with patient health encounters with an entity;
determine, as output from the program engine that executes the scoring program via the score card application, an entity score for a plurality of quality measure categories used for evaluating performance of the entity based at least on an amount of completion of the quality measure categories,
determining the amount of completion of the patient health categories from corresponding data from the population records of the entity over a defined time period;
wherein the entity score is determined using a user-defined target score for the plurality of quality measure categories and by assigning a quantity of points to the entity for the plurality of quality measure categories within the defined time period based on the corresponding data from the population records;
obtain, as output from the program engine, the entity score for the entity, an opportunity index value, the plurality of quality measure categories used for evaluating performance of the entity via the scoring program, and the user-defined target score; and
generate a graphical user interface that displays:
the entity score;
a graphical representation of the entity score as a percentage of
completion for each of the plurality of quality measure categories used in the scoring program to evaluate performance of the entity with respect to the plurality of quality measure categories; and
for at least one quality measure category of the plurality of quality measure categories, another graphical representation of the opportunity index value that is specific to at least one quality measure category, the opportunity index value indicating a specific percentage increase to the entity score that will result from the entity performing one or more tasks that correspond to the at least one quality measure category, wherein the specific percentage increase to the entity score is determined by the scoring program executed by the program engine.

17. The system of claim 16, wherein the graphical representation of the entity score is displayed in a first display area.

18. The system of claim 17, wherein the another graphical representation of the opportunity index value is displayed in a second display area that is different from the second display area.

19. The system of claim 16, wherein the graphical user interface that is generated via the one or more processors displays the plurality of quality measure categories as a treemap having a plurality of clustered rectangles, wherein the percentage of completion for each of the plurality of quality measure categories is displayed as overlaid on the plurality of clustered rectangles, each of the plurality of clustered rectangles corresponding to one of the plurality of quality measure categories.

20. The system of claim 19, wherein the graphical user interface that is generated via the one or more processors displays, for each quality measure category of the plurality of quality measure categories, a number of patients needed to increase the entity score by the percentage of completion that corresponds to the each quality measure category, wherein the number of patients is displayed as overlaid on one of the plurality of clustered rectangles that corresponds to the each quality measure category.

\* \* \* \* \*